US006400980B1

(12) United States Patent
Lemelson

(10) Patent No.: US 6,400,980 B1
(45) Date of Patent: Jun. 4, 2002

(54) SYSTEM AND METHOD FOR TREATING SELECT TISSUE IN A LIVING BEING

(76) Inventor: Jerome Lemelson, 593 Lake Shore Blvd., Incline Village, NV (US) 89451

( * ) Notice: Subject to any disclaimer, the term of this patent is extended or adjusted under 35 U.S.C. 154(b) by 0 days.

(21) Appl. No.: 09/541,299

(22) Filed: Apr. 3, 2000

Related U.S. Application Data

(60) Division of application No. 08/915,356, filed on Aug. 20, 1997, now Pat. No. 6,058,323, which is a continuation-in-part of application No. 08/743,794, filed on Nov. 5, 1996, now Pat. No. 5,845,646.

(51) Int. Cl.[7] .............................................. A61B 17/32
(52) U.S. Cl. ........................ 600/478; 600/104; 604/22
(58) Field of Search ................................ 600/407, 478, 600/585, 104, 182; 606/159, 170; 604/22, 264

(56) References Cited

U.S. PATENT DOCUMENTS

| | | | |
|---|---|---|---|
| 4,725,207 A | * | 2/1988 | Buchwald et al. |
| 4,895,560 A | * | 1/1990 | Papantonakos ............... 604/22 |
| 5,445,155 A | * | 8/1995 | Sieben |
| 5,868,767 A | * | 2/1999 | Farley et al. |
| 5,895,402 A | * | 4/1999 | Hundertmark et al. |
| 5,925,055 A | * | 7/1999 | Adrian et al. ................ 606/159 |
| 6,056,743 A | * | 5/2000 | Ellis et al. ..................... 600/15 |
| 6,129,698 A | * | 10/2000 | Beck |

* cited by examiner

Primary Examiner—Shawna J Shaw
(74) Attorney, Agent, or Firm—Niro, Scavone, Haller & Niro

(57) ABSTRACT

A computerized imaging system (such as CAT scan, MRI imaging, ultrasound imaging, infrared, X-ray, UV/visible light fluorescence, Raman spectroscopy or microwave imaging) is employed to sense the position of an endoscopic treatment system within the body of a patient. In a preferred embodiment, the system provides real-time computer control to maintain and adjust the position of the treatment system and/or the position of the patient relative to the treatment system; and also provides (if desired) real-time computer control of the operation of the treatment system itself. Other embodiments include a steerable catheter system having a rotatable abrasive member actuated by an external magnetic field.

2 Claims, 14 Drawing Sheets

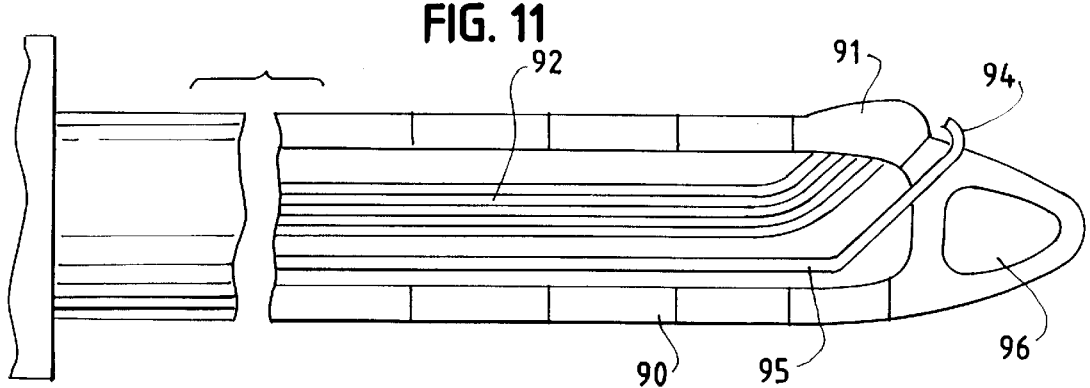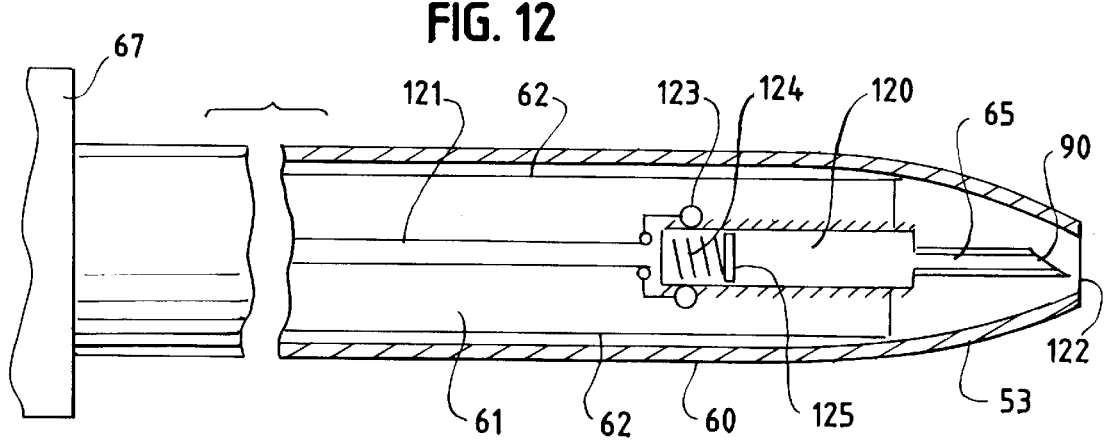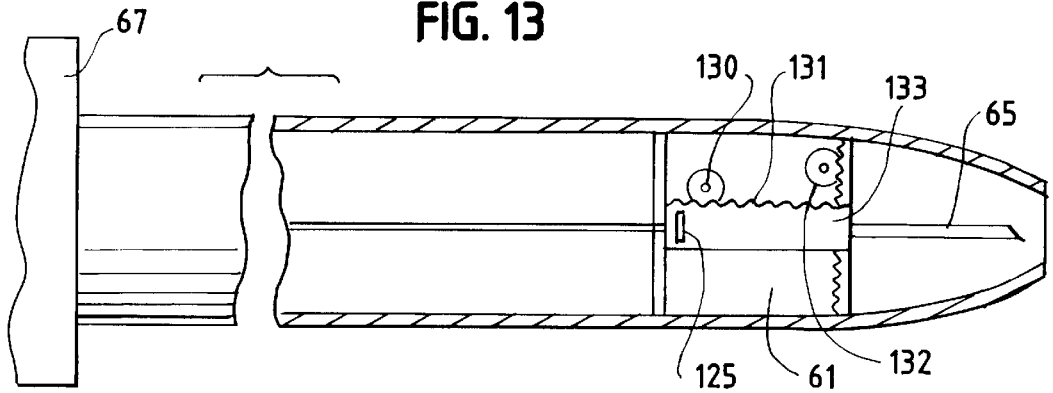

FIG. 19
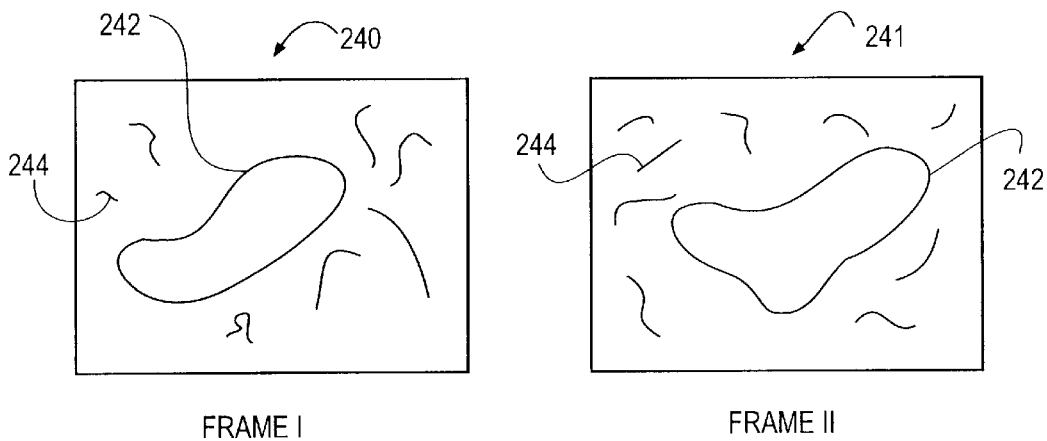
FRAME I    FRAME II
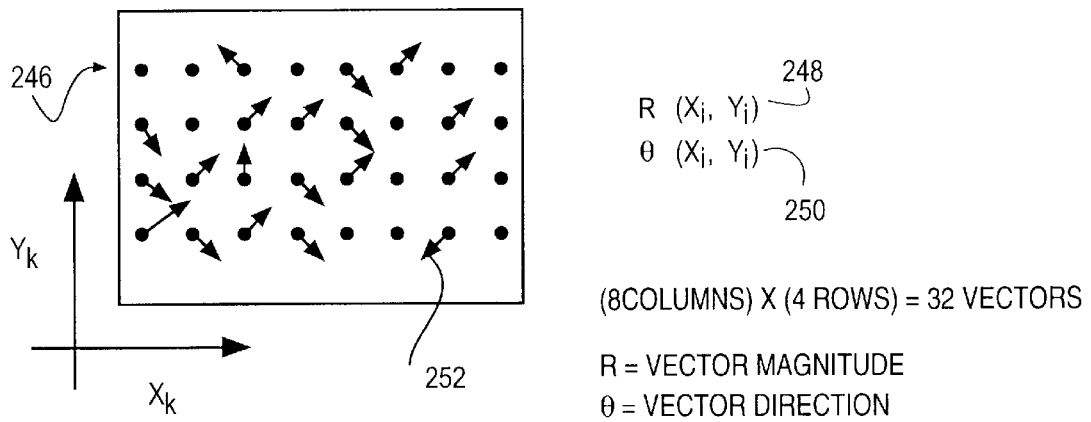
R $(X_i, Y_i)$ — 248
θ $(X_i, Y_i)$ — 250
(8 COLUMNS) X (4 ROWS) = 32 VECTORS
R = VECTOR MAGNITUDE
θ = VECTOR DIRECTION
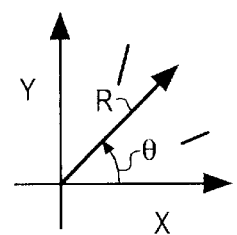

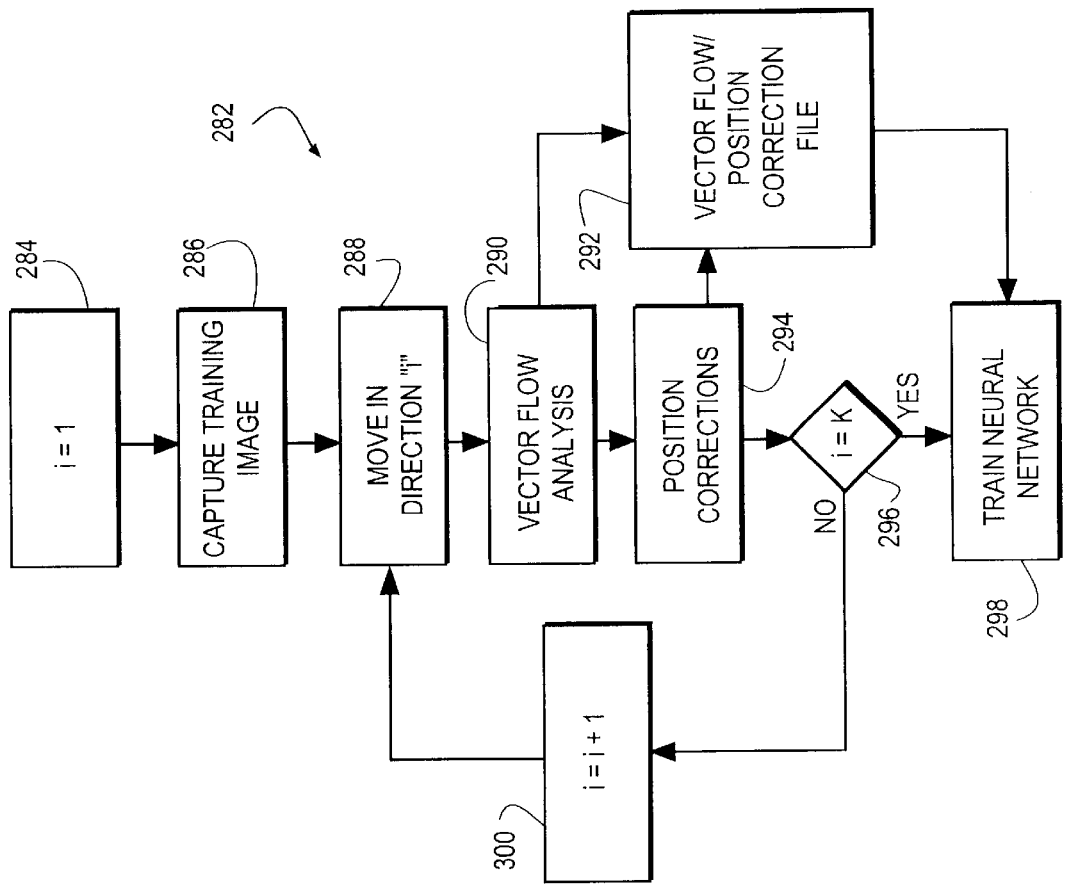
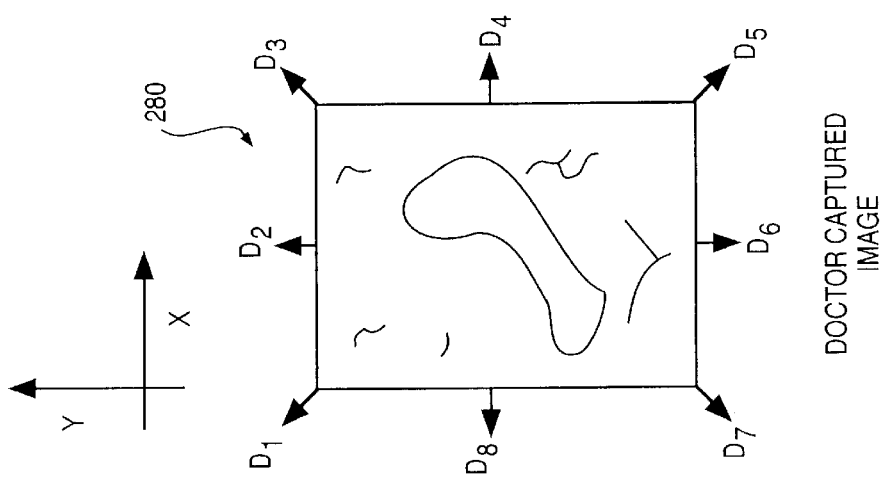
FIG. 21

FIG. 24
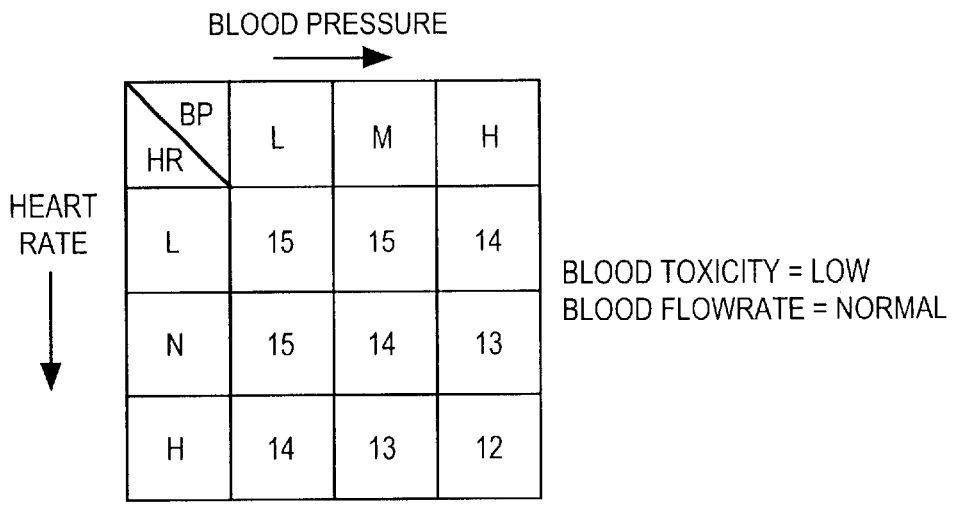
BLOOD TOXICITY = LOW
BLOOD FLOWRATE = NORMAL
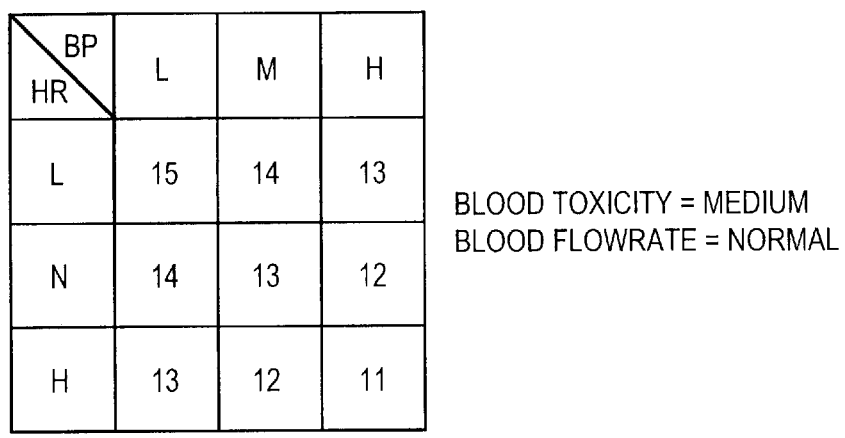
BLOOD TOXICITY = MEDIUM
BLOOD FLOWRATE = NORMAL
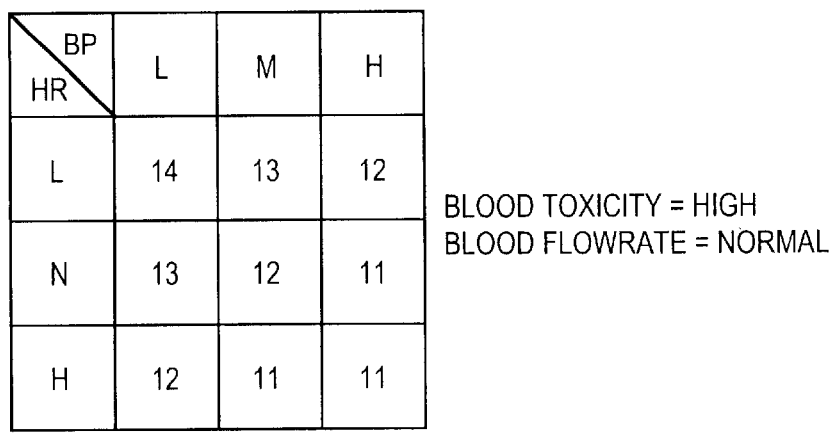
BLOOD TOXICITY = HIGH
BLOOD FLOWRATE = NORMAL

SYSTEM AND METHOD FOR TREATING SELECT TISSUE IN A LIVING BEING

This application is a divisional of Ser. No. 08/915,356 filed Aug. 20, 1997 now U.S. Pat. No. 6,058,323 is a continuation in part of application Ser. No. 08/743,794, filed Nov. 5, 1996 now U.S. Pat. No. 5,845,646 issued Dec. 8, 1989.

BACKGROUND OF THE INVENTION

1. Field of the Invention

This invention relates to systems for endoscopic treatment of select tissue in living beings (humans or animals) using real-time computer control to visualize, to position and (if desired) to operate drug dispensing, sampling (biopsy); imaging, testing and/or treatment devices within the body of the patient. The invention employs a computerized imaging system (such as CAT scan, MRI imaging, ultrasound imaging, infrared, X-ray, UV/visible light fluorescence, Raman spectroscopy or microwave imaging) to sense the position of an endoscopic treatment system within the body; and, in a preferred embodiment, provides real-time computer control to maintain and adjust the position of the treatment system and/or the position of the patient relative to the treatment system; and also providing (if desired) real-time computer control of the operation of the treatment system itself. Types of treatment systems suitable for use in the invention include surgical tools and tissue manipulators, devices for in vivo delivery of drugs in solid or liquid form; angioplasty devices; biopsy and sampling devices; devices for delivery of RF, thermal, microwave or laser energy or ionizing radiation; and internal illumination and imaging devices, such as modified catheters, endoscopes, laparoscopes and the like instruments, or a combination thereof.

2. Background of the Invention

A variety of endoscopic treatment devices exist, including those containing viewing or imaging systems; devices for endoscopic surgery (such as laser angiosurgery, as in U.S. Pat. No. 5,496,305 (Kittrell, et al.)); biopsy devices and drug delivery systems such as my U.S. Pat. Nos. 4,900,303 and 4,578,061. Typically, however, such systems are designed to be manually deployed and positioned by a surgeon and assistants. Surgical personnel must not only treat the patient (i.e., perform the surgical procedure; interpret the images or diagnostic data or obtain the biopsy sample) but also simultaneously maintain the endoscopic device such as a catheter in position (sometimes with great precision) and operate any mechanisms in the device as well, all manually working through a catheter support tube assembly which, desirably, should be as small in diameter as possible to minimize trauma during insertion and operation.

In many diagnosis and treatment situations, precise, real-time positioning of the distal (working) end of the catheter is the key to success with delivering microdoses of drugs that may have high toxicity (e.g. chemotherapeutic agents) as well as directing ionizing radiation or microwaves precisely at the tissue to be altered or destroyed, while minimizing trauma to surrounding, healthy tissue. Precise control of position is also useful in sampling (biopsy) situations to allow samples to be taken from the correct locations within the body.

Nevertheless, internal steering mechanisms for catheters (not to mention real-time control of their position within the body, which is effectively unknown) have been comparatively crude. Catheters, endoscopes, etc. have to be very long and thin, and usually are rather stiff (at least over part of their lengths) to enable them to be advanced through body ducts or directly into tissue without buckling. (Sometimes a removable "split sheath" introducer is used during implantation, and is then split and pulled away from around the catheter, leaving a very pliable catheter in place but incapable of further forward advancement. But, such pliable catheters typically cannot be steered at all, once in place, except for some limited rotation from the outside of the body.)

Steerable or positionable catheters typically are rather stiff (and correspondingly traumatic). They may use one or more off-axis pull wires to deflect the distal tip of the catheter by 20° or 30°. The pull wire or wires are fixed at the distal tip of the catheter and extend back to the proximal end. When pulled, they generate off-axis longitudinal forces that deflect the tip toward the side of the catheter where the wire is being pulled. Sometimes, as in U.S. Pat. No. 5,531,677 (Lundquist), only one off-center pull wire is used, in combination with a stiff backbone 180° away, and ribs that make the torque tube preferentially flexible toward the pull wire. (See FIG. 5 of the '677 patent; the pull wire is at reference numeral 48; the backbone is at 32 and the slots 30 between the ribs produce preferential flexibility, creating the arc shown when the wire is pulled. Return forces may be provided by an internal coil spring.)

Another system is shown in U.S. Pat. No. 5,531,687 (Snoke, et al.). In that reference, two diametrically opposed pull wires 201 and 202 are wrapped around a central drum or wheel in the handle; rotation of the wheel produces deflection at the tip towards whichever wire is pulled. This permits some limited tip movement in either of two opposite directions (though not in any intermediate directions).

U.S. Pat. No. 4,983,165 (Loiterman) uses an internal guide wire (for stiffness and to prevent buckling) in combination with a plurality of externally-inflatable pouches to force the distal end of a catheter towards (or away from) one wall of a body duct. See FIGS. 4–6 of the Loiterman '165 patent. This arrangement allows the user of a catheter which is passing through a body duct to select one branch of the duct. Such an arrangement would not be usable, however, for a catheter advancing through soft tissue.

U.S. Pat. No. 5,545,200 (West) shows another pull-wire arrangement, in which the pull wire 58 is opposed by a longitudinally-advancable "stiffener member 68" (see FIGS. 3A and 3B). By longitudinally advancing or retracting the stiffener member, the point where curvature begins can be adjusted.

Another approach to adjusting the point of curvature is shown in U.S. Pat. No. 5,533,967 (Imran). The Imran patent shows a central shape-memory element 57 which is made of a shape-memory material, such as Nitinol, which straightens out when heated (as by direct electrical resistance heating) and which is more flexible when not heated. Imran discloses moving an annular "selective conductive bypass means 66" longitudinally along the shape-memory element. Where the bypass means covers (and electrically contacts) the shape memory element, current flows through the bypass rather than through the memory element. In that region, therefore, there is less or no electrical heating and that part of the shape memory element is very flexible. Thus, when one or more pull wires are actuated, the point of flexure occurs at the place where the bypass means has been positioned. Imran also suggests that a plurality of elongate elements 41–43 "having a negative coefficient of [thermal] expansion" could be used in place of moving pull wires to generate the forces needed to cause tip deflection.

Similarly, catheters that are used for imaging typically also must be introduced and positioned manually. Moreover, they lack facility for independently rotating or positioning the sensing or imaging element independently of the manipulating or treatment device in order to focus on a specific area of tissue being treated by drugs, mechanical manipulation or other means. U.S. Pat. No. 5,435,805 (Edwards, et al.), for example, discloses various embodiments of a probing head and, in one embodiment, dual optical lenses (see FIG. 8). Embodiments in FIGS. 15–20 show a needlelike element that is termed a "stylet" or "stylus" for penetrating tissue, such as a prostate, to apply microwave or RF treatment. At column 6, lines 56–60, it is stated that the device can be used in a variety of ways including to deliver liquid (i.e., drug). Positioning of the overall catheter is manual, by means of a torque tube assembly.

U.S. Pat. No. 4,967,745 (Hayes, et al.) discloses a polished end fiber optic cable bundle that forms a lens. A computer control system is adapted to locate healthy or diseased tissue using spectral imaging techniques, and to control a laser to fire pulses of laser radiation down one or more optical fibers to destroy arterial plaque while avoiding damage to healthy tissue. Inflatable balloons inside the catheter, or control wires, may be used to deflect the fiber optic bundle within the catheter. The catheter itself, however, is manually introduced and positioned.

Still further techniques for steering a catheter within the body by altering its shape are disclosed in my co-pending application serial no. 08/662,345 (filed Jul. 12, 1996) now Pat. No. 5,800,421 (issued Sep. 1, 1998), the disclosure of which is incorporated herein by reference. These techniques utilize electrosensitive gels to alter the rigidity or shape of a catheter.

The prior art approaches, however, are deficient in a number of particulars. They require not only manual introduction, but also more or less constant manual adjustment of position and often of operation. Almost everything is done by hand: the surgeon works by feel, with rudimentary or no imaging capability to guide him and no active computer control to take over so he can concentrate on the operation instead of positioning the catheter and keeping it in position. This increases the number of surgical personnel required, and distracts them from the procedure or diagnosis in progress.

Prior art devices typically also reflect the premise that forces used to alter the shape of the catheter have to be generated and exerted from within the lumen or lumens of the catheter itself (such as by pull wires). Since catheters, endoscopes and other devices, for use inside the body are usually long and thin. This automatically creates problems in obtaining a favorable mechanical advantage for forces that one wants to exert normal to the axis. (In other words, it is necessary to pull the wire(s) very hard in order to generate only a moderate amount of sideways force, since the fulcrum point typically is far back from the area where a bend is desired.)

BRIEF DESCRIPTION OF THE DRAWINGS

FIG. 11 shows a steerable catheter system suitable for computerized positioning control, that is actively positioned using an externally-applied magnetic field.

FIG. 12 shows a steerable catheter system suitable for computerized positioning control including an extendable, rotary member supporting a drug injection assembly.

FIG. 13 shows a catheter system suitable for computerized positioning control including a steerable drug injection mechanism actuated by micromotors.

FIG. 19 shows an exemplary two-dimensional vector space illustrating changes in measured physiological variables related to patient condition.

FIG. 21 shows one method of training the neural network controller using simulated departures from the nominal (controlled) values of measured variables.

FIG. 24 illustrates example fuzzy inference rules for ranges of the fuzzy logic variables of FIG. 23.

SUMMARY OF THE INVENTION

Figure 1:
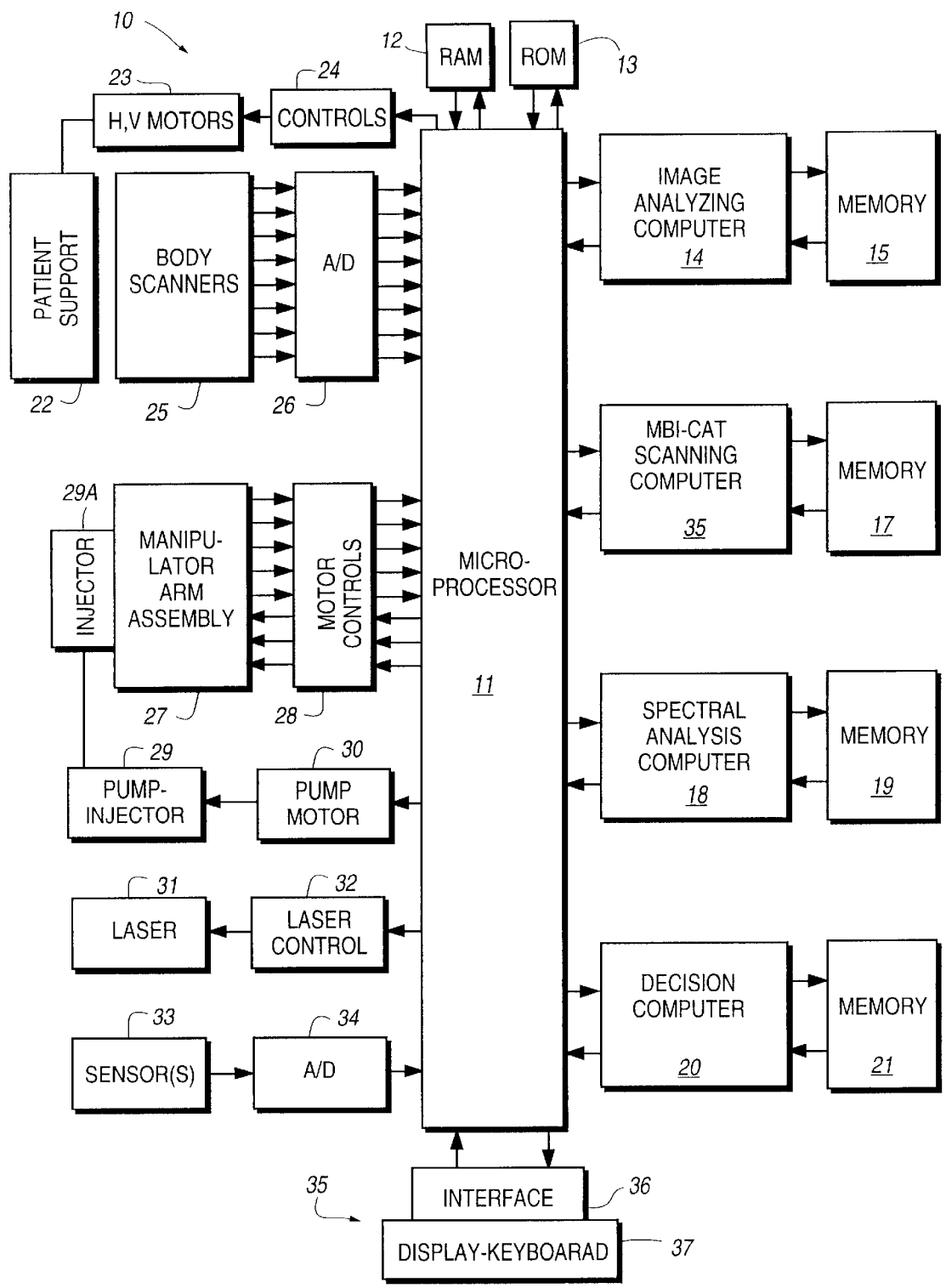
FIG. 1 shows one type of computer control system suitable for real-time positioning of an endoscopic treatment or diagnosis system (such as a catheter) within the body.

My invention provides a system and method for real-time, interactive computer control of the position of catheters, laparoscopes and/or endoscopic devices, enabling surgical personnel to exercise more precise control over the location of such devices. Novel methods of steering such devices within the body, and of delivering aliquots of drugs to precise, selected locations within the body also are disclosed. In addition, devices for the burning or ablation of surrounding tissue (as for example, during angioplasty procedures) are disclosed.

It is an object of this invention to provide a method of precise, real-time computer control of medical instrument or catheter position within the body, preferably using a feed-forward backpropogation neural network or a Hopfield neural network, capable of unsupervised learning, to observe the path of catheter introduction and learn the appearance of the surrounding tissue (and the appearance of the desired location using, for example, a Kohonen feature map) during the catheter introduction procedure; and to control the position of the catheter thereafter despite ongoing changes in the shape and appearance of surrounding tissue.

It is a further object of this invention to provide improved steerable catheters whose shape can be changed within the body.

Still another object of this invention is to provide steerable catheters having minimal or no interior steering equipment, thus minimizing their size and therefore trauma to a patient.

It is another object of this invention to provide steerable catheters and the like equipped with controllable drug-dispensing devices.

It is yet another object of this invention to provide a steerable catheter capable of viewing internal tissue and structures within the body.

It is another object of this invention to provide catheters that can deliver light or radiation to select tissue within the body using various scanning patterns.

These and other features, objects and advantages of my invention will be apparent upon consideration of the following detailed description of my invention.

DETAILED DESCRIPTION OF THE PREFERRED EMBODIMENTS

Computer Positioning Control

The present invention can employ imaging and computerized image analysis techniques based on sensors located external to the body (such as X-rays or Magnetic Resonance Imaging (MRI) sensors); images and coded image information derived from visual electro-optical sensors placed inside the body through a lumen of the catheter, or a combination of both types or still other of sensing systems or techniques. A variety of computer control systems can be used; one example appears in FIGS. 1 through 3. Another example of neural network control appears in FIGS. 18 through 24.

The present invention will be described in terms of controlling a catheter, but it will be understood by those of ordinary skill that endoscopes, laparoscopes, surgical instruments and other devices for insertion into the body of a patient also can be used.

Generally speaking, the location coordinates of select tissue of a living being in which a catheter-based operation is to be performed, are defined or computed with respect to images of the patient's anatomy showing anatomical structures which may be generated, for example, by employing computerized axial tomography (CAT scanning), magnetic resonance imaging (MRI), ultrasonography, positron emission tomography (PET), infrared, X-ray or microwave imaging, or other types of electronic scanning from sensors placed outside the body. In accordance with the present invention, a computed image of a select anatomical area is generated by using one or more of the conventional imaging modalities mentioned above, and a location coordinate with respect to a patient support structure is assigned to each pixel making up the image. The anatomical region into which it is desired to perform a catheter-based operation, such as injection of a drug, is then located on the electronically generated image or images by a radiologist, for example, with selected of the pixels making up the image of the region serving to define the transplant location. A preferred means by which this can be performed is to display the images of the catheter and the select anatomical region of the body on a display monitor having a manually positionable cursor for outlining an area containing the desired anatomical region. The operator of the system then inputs to a computer, digital data in the form of codes defining the anatomical location at which an operation is to be performed, as represented by the select pixels within the outlined area. As described below, each pixel of the body or organ image displayed by the computer has assigned to it a set of location coordinates calculated or defined with respect to a structure such as a table supporting the patient while the imaging is performed (see FIGS. 2 and 3, discussed below). The same or a similar patient support structure is then utilized during the catheterization procedure. The catheter is moved manually or by the manipulator under computer control, inserted into select tissue, and operated so as to perform the desired operation at select location coordinates with respect to the support structure.

To facilitate use, crosshairs may be projected onto the screen and a mouse or other pointing device may be used to provide positioning instructions. When used with catheters containing fiber optic bundles (see below), one or more strands of the bundle may be used to project a beam of laser light onto surrounding tissue for aiming purposes, while the remaining fibers are used to transmit images.

To facilitate pinpointing of the catheter position, a variety of devices may be used depending on the sensing modality. In the case of ultrasonic sensing, for example, a closed cavity in or near the distal end of the catheter (or at some other location along the length of the catheter that must be pinpointed with precision) acts as a resonator to make the location appear clearly on the ultrasonic image. In the case of X-ray or MRI sensing, metal foil inserts or electronic circuitry can serve the same function. Active RF antennas also can be included at the desired point(s) inside the catheter.

In one embodiment the patient is required to be in the same position with respect to the support structure during both the imaging and catheterization procedures, so that the location coordinates selected will correspond to the proper anatomical region of the patient. One way of accomplishing this is to use a patient support structure having a moldable support structure defining a surface that can be made to conform to the shape of the patient's body as a kind of body cast. Once such a body impression is made, the patient may be placed in substantially the same position on the support structure for both scanning/imaging and subsequent transplantation procedures. Such a moldable patient support may also serve to immobilize the patient during both procedures. Other patient restraint devices, such as straps and adjustably positionable table stops, may also be employed.

The manner of assigning location coordinates to each image pixel depends on the particular imaging modality. For example, with a conventional CAT scanner, the x-ray tube emits a narrow beam of x-rays toward the patient with an x-ray detector, such as an array of scintillation detectors, positioned on the opposite side of the patient on which an x-ray shadow is formed. The x-ray tube and detectors, mounted on a rigid gantry, are rotated in multiple steps about the body until an entire axial slice is viewed from multiple angles. Codes defining the date acquired by the scintillation detectors are entered into a computer which uses mathematical algorithms to reconstruct a cross-sectional image or images of slices of the region examined. Such a computerized scanning arrangement calculates the degree to which the tissue interposed between the x-ray tube and the detectors absorb the x-ray beam and thereby provides an attenuation coefficient for each area of tissue examined. Essentially, the quantity of x-ray absorbed in small volumes (voxels) of body tissue in the slice is computed. Computer analysis of the image signals and data collected then allows assignment of a numerical value to each small area (pixel) of the cross-sectional plane. By means of a digital-to-analog converter, the numerical value of each pixel is translated to a gray scale for driving a CRT display or the like and may be employed for automatic control.

Due to the nature of the CAT scanning image reconstruction algorithm, the computer necessarily must assign location coordinates to each pixel with respect to the x-ray detector in order to generate the displayed image. Such coordinates are computed with respect to the patient support structure in the axial plane which is being imaged. In order for such coordinates to be useable for properly directing a transplantation or other tool in accordance with the present invention, however, they must be scaled and combined with another coordinate along the axial axis. In order to assign an axial location coordinate with respect to the patient support structure for each pixel, the positions of the x-ray tube and detector with respect to the patient support surface are sensed, and digital signals are generated that are input to the computer during the imaging procedure. The location coordinates for each pixel making up the image with respect to the patient support structure may be then readily calculated.

In pulse-echo ultrasound techniques, an ultrasonic pulse is transmitted through the body tissues with the reflected echoes from each acoustical interface sensed by a transducer in order to provide a train of digital signals that define an image of the underlying structure. In so-called B-mode ultrasound, the pulse-echo procedure is performed in scanning manner to provide signals for imaging the underlying morphologic structures in a tomographic format. The resulting scanning signals, after digitization, are used by electronic circuitry to construct a two-dimensional array of pixel values for driving a display. In order to construct an image, each pixel is assigned a coordinate location with respect to the transducer in the same plane at which the ultrasound is emitted; Conventional ultrasonic scanning, however, requires that the ultrasonic transducer be contacted or coupled to the body surface over the region to be examined and positioned so as to scan at various angles. In order for the computer to compute the location coordinates for each pixel making up a display of an ultrasonic scan, the transducer is mounted on a movable arm having sensors in its joints for producing signals proportional to the degree of flexion or rotation of each such joint, which sensors generate signals that are then fed to the computer for calculating the arm's position and orientation. Using appropriate scaling factors, the location coordinates for each pixel making up the image with respect to the patient support means may be readily calculated by a computer supplied with the above-mentioned data.

Computerized image construction in conventional MRI scanners, for employment in the present invention, is similar to that used in CAT scanners in that intensity values for an array of pixel values are computed with each pixel value stored in the computer being assigned a set of location coordinates in order to generate the reconstructed image. In MRI scanning, nuclei such as protons are subjected to a magnetic field gradient, called the slice-select gradient, which varies along the axis perpendicular to the plane of the image. Certain protons (such as hydrogen nuclei of water molecules in the tissue being scanned) within the magnetic field gradient are excited to resonance by a so-called 90 degree RF pulse which causes them to emit detectable radiation. The amplitude and frequency of such emitted radiation is used to assign proton density values to pixels and generate the MRI image. The location coordinates of each pixel in the image are calculated with respect to the patient support structure within the plane of the image cross-section, assuming the receiver coil of the MRI scanner remains at a fixed distance from the patient support structure. In order to derive an axial coordinate value (i.e., along an axis perpendicular to the plane of the cross-sectional image) for each pixel, it is necessary for the computer to compute the distance along the slice-select gradient with respect to the patient support structure, where the Larmor frequency of the excited nuclei corresponds to the frequency of the 90 degree RF pulse. Such a computation only requires that the computer be supplied with data reflecting the magnitude of the slice-select gradient field versus distance and the frequency of the RF pulse which can either be assumed to be in accordance with computer command or can be sensed by magnetometers and a separate RF receiver coil. MRI scanners also allow the particular gradient fields to be generated along arbitrarily chosen axes so as to produce images no only in the transverse plane but also in coronal, sagittal, and oblique planes. The axial coordinate for each image is then computed in the same way as just described, but the coordinate is then along an axis perpendicular to the plane of the cross-sectional image. Finally, since the patient support structure and the MRI imaging apparatus are relatively moveable with respect to one another, the computer is fed with data produced by position sensing means so that the location coordinates can be translated so as to be with respect to the patient support structure.

Once the location coordinates defining the select body region at which it is desired to perform the catheterization operation have been calculated by the computer, the catheter is inserted (either manually by surgical personnel or under computer control by robot manipulators) and the catheterization operation (for example, select drug injection) is performed. The process may then be repeated at different sites in the select body region. As will be described more fully below, electro-optical sensing and monitoring means may be provided, allowing the effects of the catheter operation to be monitored by the computer and the results of such monitoring may be used to control further injections.

FIG. 1 shows a computer system 10 for effecting the automated performance of a catheterization procedure in accordance with my invention. The catheter may be automatically positioned with respect to the patient by means of a multiple axis electro-mechanical manipulator which is controlled in its operation by coded control signals generated as a result of scanning that portion of the patient's body where it is desired to effect the particular catheter operation such as angioplasty, drug delivery or other operations. A catheter may be similarly directed under computer-control to an intraductal or other internal body site. Alternately, the catheter may be introduced manually using any of a number of known techniques including Seldinger insertion or the use of a split-sheath introducer, with the aid of control signals generated by the computer analysis of a real-time computer image of the location and path of the catheter, or its operating end or head.

The scanning signals may be generated by one or more known scanning devices, such as a nuclear magnetic resonance (NMR or MRI) scanning system, a computerized axial tomography (CAT) scanning system employing x-ray scanning, a PET scanning system, various infrared scanning systems operable to generate image signals of tissue and bones, or ultrasonic pulse-echo scanning systems. Such scanning signals may be computer processed and analyzed to generate multiple cross-sectional views such as parallel slice images of the portion of the body where it is desired to operate. The image information defined in the cross-sectional views or slices of the body tissue may be digitized to generate trains of digital (picture) signals which are analyzed by a computer wherein resulting code signals are generated defining the borders of the anatomical structures and which may be further computer processed to provide further code signals indicative of coordinate locations of those structures. Such coded information may be used by the computer to control the operation of an automatic multi-axis manipulator for a catheter device, such as a heated scalpel, a hollow needle or ablation device, a rotary cutting tool, etc., to automatically position and insert the catheter, guide it to pass through intervening tissue or body ducts to reach the specific location where the catheterization operation is to be performed.

Alternatively, the computer control system may simply observe the manually-controlled passage of the catheter to the desired location, using the scanning system. Advantageously, a control algorithm utilizing a layered feedforward backpropagation neural network or a Hopfield neural network (or a combination of both) may be used. A Hopfield network, which can be arranged so as to be able to compare the pattern of approach to the desired location chosen by the surgeon and thereby "learn" the pattern of movement required to maintain the desired location against changes in position of the catheter or the patient caused by breathing, muscle contraction, etc. By minimizing the Hamming distance between the actual location at a given time and the "learned" location set by the surgeon during introduction of the catheter, the computer control system can effectively maintain the catheter position despite ongoing changes in the image of the location caused by physiological changes in the patient's tissue during the catheterization procedure.

Figure 2:
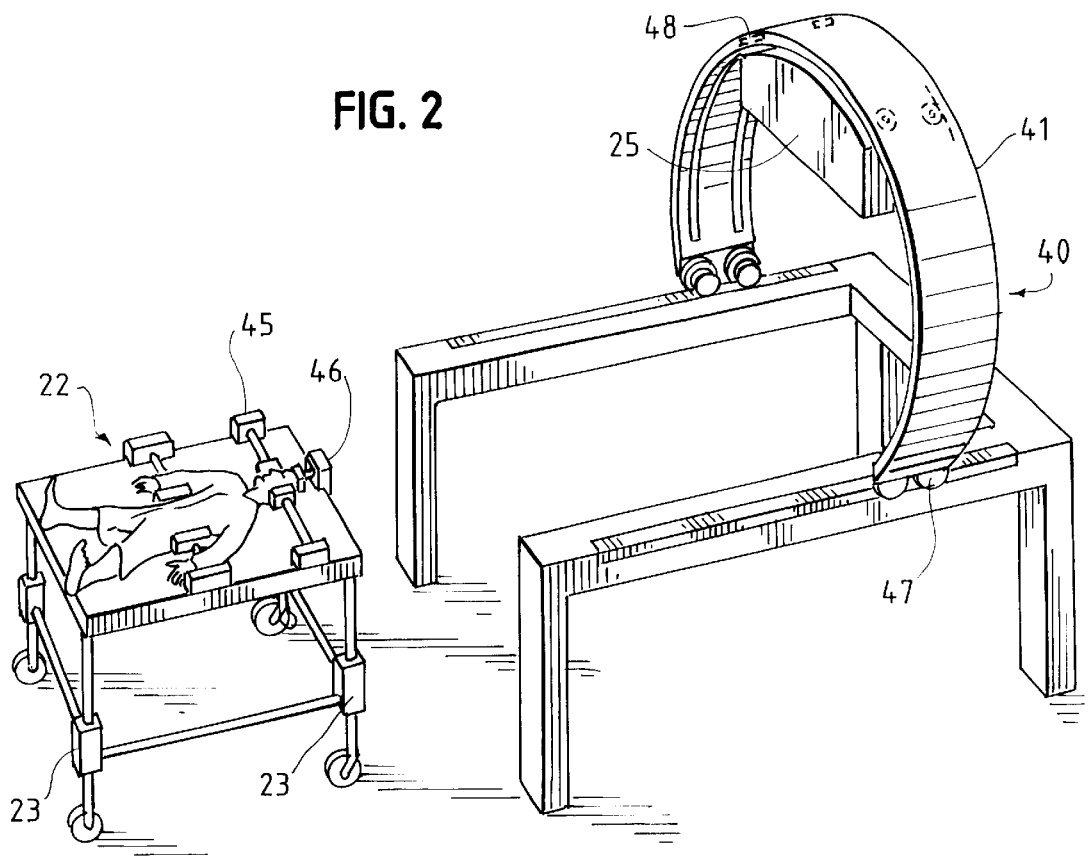
FIG. 2 shows a patient orientation system which optionally can be used to help control the position of the endoscopic device within the body.
Figure 3:
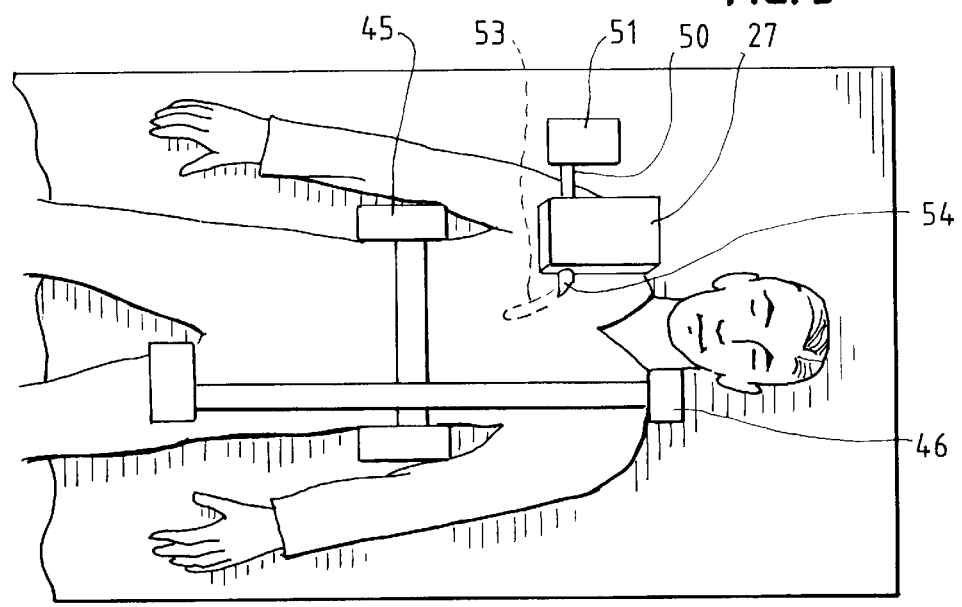
FIG. 3 shows further detail of a patient orientation system which optionally can be used to help control the position of the endoscopic device within the body.

System 10 includes a number of computers, devices and subsystems which are automatically controlled in their operation or generate feedback information in the form of signals passed through a control computer or microprocessor 11. (Preferably, such feedback information is processed using an appropriate backpropagation function and presented to the output layer and/or the hidden layers of a neural network used to control catheter position.) An image analyzing computer 14 with an attendant programmable memory 15 analyzes image information generated by an NMR or CAT scanning computer 16 with attendant memory 17 which receives digitized image information from a plurality of MRI sensors 25 which can scan or sense a select portion of the body of a patient held immovable against a patient support or table 22 which is motorized and driven in multi-axis movement by a plurality of gear motors 23 (see FIG. 2), the controls 24 of which are operated by trains of digital control signals passed through microprocessor 11 from either manual controls and/or one of the computers connected to the microprocessor. In addition, patient positioning motor assemblies 45 and 46 may be directly coupled to specific portions of the patient's body as shown in FIGS. 2 and 3, allowing particular parts of the patient to be moved relative to the patient support 22 to further provide fine positioning of the patient relative to the sensor and catheter. Again, one or more neural networks designed for unsupervised training may be used to evaluate and weight the effects of moving the patient support 22 in comparison with the effects of moving the patient himself using motor assemblies 45 and 46. With this approach, the computer progressively learns how best to maintain catheter position during the procedure by altering the weights used at each layer of the neural network as the catheterization procedure progresses.

Conventional CAT and MRI scanning arrangements generally rotate and axially move the patient through the scanning field. In addition, the MRI, CAT, PET body scanners or array of sensors 25 may also be supported on a mount 41 which is driven by motors 47 and 48 and controlled to move about and/or along one or more axes by means of a computer, such as a decision computer, connected to the microprocessor and operable to analyze the signals output by one or more of the computers 14 and 16 to effect control of the treatment operation and/or at least a portion of the scanning operation. The analog image signals output by the body scanners are converted to trains of digital image signals by one or more analog-to-digital converters 26 which pass such trains of signals through microprocessor 11 to the MRI or CAT scanning computer 16 for analysis and conversion to useable image information for use by the image analyzing computer 14.

In one preferred embodiment, a catheter positioning manipulator 27 is supported adjacent the patient support 22 to which it is preferably connected. The catheter positioning controller/manipulator 27 is driven by a plurality of gear motors or hydraulic or electromechanical positioners (not shown) which are used to manipulate the proximal end 50 of the catheter outside the insertion point 54, thereby affecting the location of the distal end 53 of the catheter. As more fully described below, such manipulation of catheter may include simply movement of the proximal end of the catheter; it may also include manipulation of the catheter shape within the body using various types of steering mechanisms.

As in the case of the patient positioning devices, one or more neural networks designed for unsupervised training may be used to evaluate and weight the effects of moving the patient support 22 in comparison with the effects of moving the proximal end of the catheter; manipulating the steering mechanism (if any) by using catheter steering controller 51; and moving the patient himself using patient positioning motor assemblies 45 and 46. With this approach, the computer progressively learns how best to maintain catheter position during the procedure by altering the weights used at each layer of the neural network as the catheterization procedure progresses.

The control signals generated thereby are sent to a bank of controls 28 which receive and pass direct command control signals from the computer 20 and apply feedback signals from the various manipulator motors to effect a suitable degree of precision operation of the catheter while its operating head is in alignment with select tissue to be treated or operated upon.

As described more fully below, a sensor or sensor array 33 may be located in the catheter at or adjacent its distal end 53 and may be operable to receive light reflected from tissue adjacent the end of the catheter. An optical fiber light pipe may extend from the output of the laser 31 through and to the open end of the catheter to conduct laser light to tissue adjacent the open end of the catheter while a second optical fiber may extend from such open end, back up another light pipe in the catheter to the sensor 33. Resulting spectral radiation emitted by the tissue intersected by the laser radiation is passed to the end of the optical fiber adapted to receive same and back along such fiber to the photodetector at the other end thereof which generates an analog electrical signal modulated with spectral information relating to the tissue intersected by the laser light. Spectral information such as Raman spectra can be used to analyze and detect or diagnose the tissue and to distinguish plaque deposits from healthy tissue at the walls of blood vessels, for example.

Also shown connected to the control computer or microprocessor 11 via an interface 36 is a computer 35 such as a workstation or PC which includes a display and a keyboard which is operable to input data to the RAM 12 or any of the computers 14, 16, and 18 or to control the operation of the manipulator 27, pump motor 38 and laser 31 or a plurality of such subsystems and devices for performing the described treatment or surgical operations. It is noted that the pump 29 may be varied in its operation in accordance with the control signals generated by the decision computer 20 to a controller for such motor to predetermine the quantity and rate of flow of transplant medium and/or medication pumped to the injector 29A after its injection tube or tubular needle has been driven under computer control to a select location with respect to select tissue. A plurality of pumps, such as pump 29, may be operated by respective pump motors and may be provided mounted on the operating head of the manipulator, each of which pumps is operable to force flow a different medical material from a respective of a number of reservoirs to the needle or tube of the injector 29A or to separate injectors therefor.

System 10 may also be operable to automatically perform auxiliary or other operations on select tissue, such as select tissue manipulation, handling, or cutting operations using one or more automatically positioned and controlled tissue grippers or cutting tools which are supported by the operating head of the manipulator 27 and controlled in powered operation to cut select tissue while gripper held or employing one or more lasers to ablate, burn or otherwise operate on such select tissue. RF energy also can be applied for such purposes, as described below.

Not shown, but assumed to form part of the computer 35 and its peripheral controllers, are manual means for effecting selective control of the described catheters, manipulators and the body tissue scanning devices, for use by medical personnel in supplementing the computer controlled operations in the performance of certain operations to detect and treat select tissue of the body. Computer controlled imaging and radar and laser range finding devices may also be employed to provide scanning signals for computer 14, to permit the computer to further analyze the image content defined by select cross-sectional views or slices generated by the CAT, PET or MRI scanning system 25, so as to automatically determine the depth location and three dimensional shape of the transplant site or a growth or growths thereat and to provide coded control signals for effecting automatic surgery on select tissue or treatment, as described. Thus the body scanning system 25 may be employed by itself to generate computer analyzable image information or may be supplemented with image information generated by an electronic camera, such as a television camera and/or by one or more laser-photodetector scanning arrangements which are fixedly supported within the catheter or which show a view from the distal end of the catheter through a fiber optic bundle.

Use of Neural Networks and Fuzzy Logic

As noted above, feedforward backpropogation or Hopfield neural networks (or a combination thereof) can be employed from the beginning of a catheterization procedure to "learn" the proper location of the catheter with respect to adjacent tissues and to continuously maintain that position against changes in position and sensed appearance of the surrounding tissue that may be caused by patient respiration, movement, and by the catheterization procedure itself.

Figure 18:
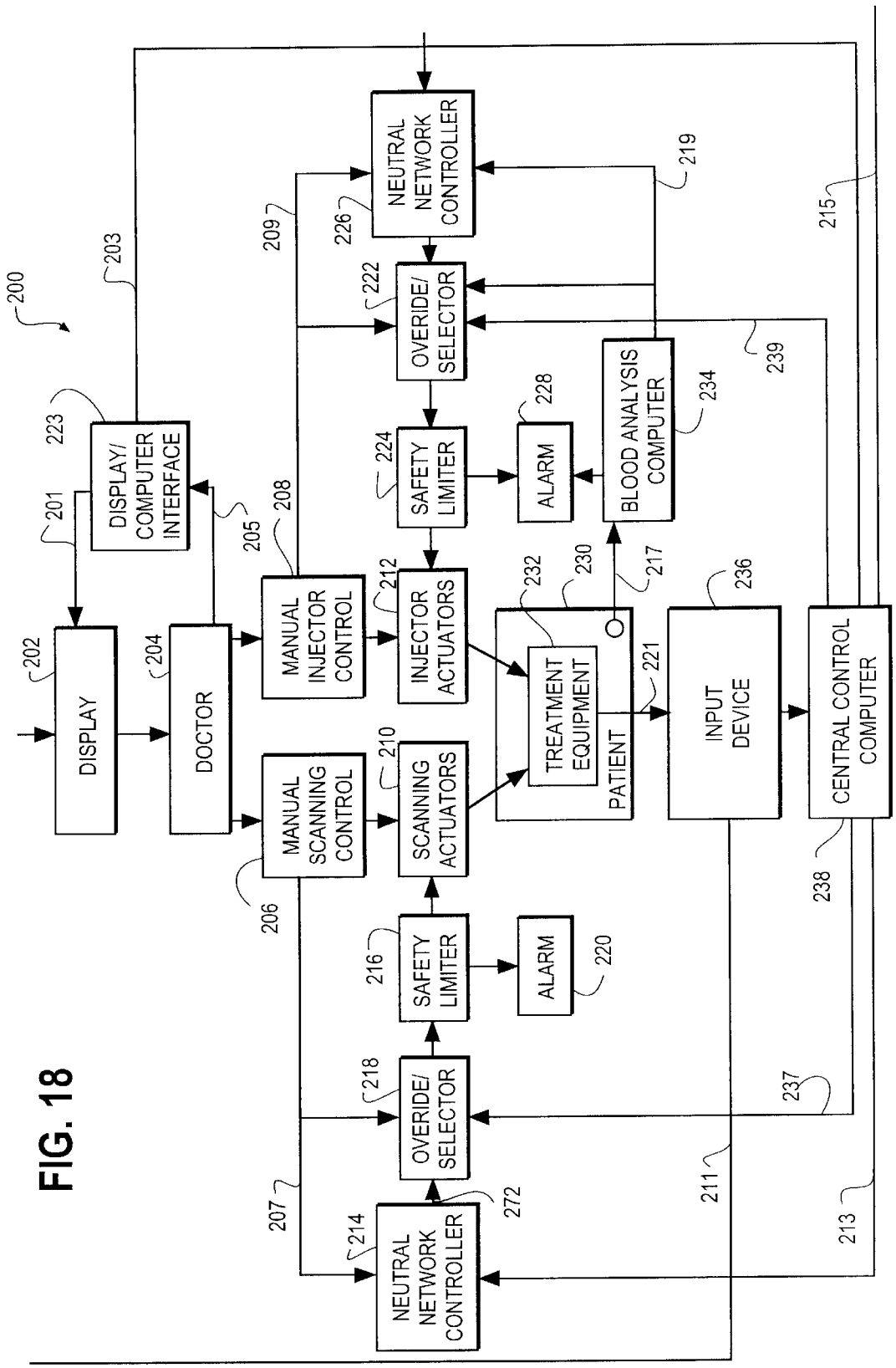
FIG. 18 illustrates a neural network and fuzzy logic control system useful in evaluating the patient's condition and selecting and implementing an optimal response strategy.

More specifically, FIG. 18 depicts a neural network and fuzzy logic controller system 200 useful in the system and method of this invention. The block diagram of FIG. 18 illustrates the interaction of the doctor 204 with computer assisted treatment modalities, including for illustrative purposes therapeutic agent injection and scanning, using (for example) one of the catheters described herein in connection with the embodiments of FIGS. 25 through 28. Neural networks and fuzzy logic are used to assist or replace the doctor in controlling injections and/or scanning. In addition, the doctor 204 may exercise direct manual control over drug injection and scanning operations. Thus, the system 200 of FIG. 18 is capable of automatic operation, computer assisted operation, or direct control by the doctor 204.

As illustrated in FIG. 18, the treatment system may include a video imaging capability as well as one or more sensing devices such as blood pressure, heart rate and blood flow measuring devices for delivery of data signals 221 to input device 236. The input device 236, in such instance, may create video signal outputs and other data outputs 211 for delivery to display 202 for viewing by the doctor 204. Thus the doctor may have direct video monitor capability for observing the patient during treatment, as well as capability for viewing other measured data. In this way, the system 200 of FIG. 18 may provide the doctor with video and data feedback to assist in scanning and proper delivery of the therapeutic agents. (It will be understood that the video images can be derived from various sensing modalities, including visible light, X-radiation, MRI, CAT, PET, ultrasound and various other sensing techniques.

In addition to the above described manual operation with video feedback, the system 200 provides central control computer 238 for analysis of signals from image input device 236 and generation of injector and defibrillator control signals for automatic operation.

The neural network controller 214 may be trained using simulated output signals from central control computer 238, manual control signals 207 from the manual control 206, or a combination of both, to generate appropriate output control signals for automatic positioning and operating control of the drug injection and defibrillator actuators 210 and 212.

Drug injection or administration (as well as other vascular access needs) can be accomplished by means of an implanted catheter (for example, a subclavian catheter). As described below, a separate lumen of a catheter used for scanning can be used. (See FIG. 25). Alternatively, a sharp cannula or needle can be attached to the patient's skin at an appropriate location and directed to puncture the skin under computer control when needed. (That method may be less suitable for intravenous injection due to the difficulty of locating a vein by remote sensing.) Jet injection of drugs using compressed air, high pressure fluid or other means are additional alternatives. Obviously, more than one drug may be available for injection if the patient's condition warrants it. In such instance, multiple injection points may be supplied, or valves and pumps may be used to infuse more than one drug through a single catheter.

The neural network output is fed to override/selector controls 218 and 222. Override/selector control 218 passes the neural network output signals to safety limiter 216. If signals received by safety limiters 216 and/or 224 are outside predetermined limits, the limiter 116 or 224 activates alarm 220 to notify the doctor or operating team of an unusual error condition. Normal signals are passed via safety limiters 216 and/or 224 to actuators 210 and 212 for drug injection and scanning. At any time the automatic control apparatus may be disabled by the override/selector controls 218 or 222, providing direct control to the doctor 204. The override/selector controls 218 or 222 are also used to disable neural network 214 output during training of the neural network.

Override/selectors 222 and 218, therefore, permit doctor 104 to deactivate automatic control of the injector and/or scanning actuators at any time, thus assuring the doctor always maintains ultimate control over the operations.

In addition to central control computer 238, optional blood analysis computer 234 may be used to analyze blood flow rates and composition from samples derived from patient 230 via line 217, which may be attached to a catheter or shunt of known design to provide access to the patient's circulatory system. The results of such blood analysis are connected via line 219 to neural network/fuzzy logic controller 226. This configuration may permit the analysis of blood flow rates and composition in addition to the blood pressure and heart rate information mentioned above. Unacceptable blood flow rates or undesired transmission of therapeutic agents by the bloodstream are detected by blood analysis computer 234 and may be used to control the rate of injection of the therapeutic agent via the neural network/fuzzy controller 226 and injector actuator 212 in the manner illustrated in FIG. 18.

It will be understood that drug injection and defibrillation are only examples of various forms of treatment suitable for implementation in connection with my invention. Among other treatments that can be applied are insulin therapy, chemotherapy, anaesthesia, anti-convulsive drugs, antihistamines and others.

Naturally, the physiological variables that will need to be monitored will vary in such instances. Blood sugar, for example, would be monitored in the case of diabetic patients.

FIG. 19 illustrates in graphic form the concept of the generation of control vectors. In FIG. 19, the patient's physiological state is illustrated by the changes between successive states 240 and 241. For illustrative purposes the axes may be considered to represent heart rate and blood pressure. Region 242 may be considered an acceptable or nominal range of the pertinent variables.

If the patient's condition changes in such a way as to place the measured combination of blood pressure and heart rate outside of acceptable region 242, the central control computer takes action to bring the two variables back into the acceptable region. Such movement may require injection of drugs or other therapy. The control computer 238 monitors changes in the patient's state as shown in FIG. 19 by a vector matrix array in an x, y coordinate system used to record the magnitude and direction of movement in the successive states 240 and 241. Illustrated in the vector field 146 are representative vectors 252 with each vector having a magnitude $R(x_i, y_j)$ 248 and a direction indicated by $\Phi(x_i, y_j)$ 250. The values for the magnitudes, R, and directions, $\Phi$ of the vectors may be computed in a number of ways using, for example, differences between successive states or gradient calculation for the movement of particular values of the state variables. In the representative example of FIG. 19, a total of 32 vectors are used, being arranged in 8 columns and 4 rows. The vectors provide an analytic numerical measure of movement in the state variables at successive times. These vectors are used as input to the neural network controller 214 in FIG. 18.

Methods of computing optic flow are known in the art of image processing; such methods can be adapted to processing of other variables such as heart rate and blood pressure in this example. The following publications, each of which is incorporated herein by reference, provide detailed explanation of optic flow computation: Barron, I.L., et. al., "Performance of Optical Flow Techniques", TR-299, Department of Computer Science, University of Western Ontario, London, Ontario, NSA 5B7, July 1993; Singh, A. "Optic Flow Computation: A Unified Perspective", IEEE Computer Society Fress, 1993. The use of neural networks for video image processing and control signal generation has likewise received considerable attention in recent years. The following references, each of which is also incorporated herein by reference, provide detailed explanations on the general configuration and operation of neural networks: Lippman, Richard P., "An Introduction to Computing with Neural Networks," IEEE ASSP Magazine, April 1987, at pp. 4–22; "Special Issue on Neural Networks II: Analysis, Techniques & Applications," Proceedings of the IEEE, Vol. 78, No. 10, October 1995; and Widrow, Lehr, "30 Years of Adaptive Neural Networks: Perception, Madaline and Back propagation," Proceedings of the IEEE, Vol. 78, No. 9, September 1990, at pp. 1415–1442; Rao, V. B. And Rao, H. V., *Neural Networks & Fuzzy Logic*, MIS Press, New York, 1995; and Chen, C. H., *Fuzzy Logic And Neural Network Handbook*, McGraw-Hill, New York, 1996.

Figure 20:
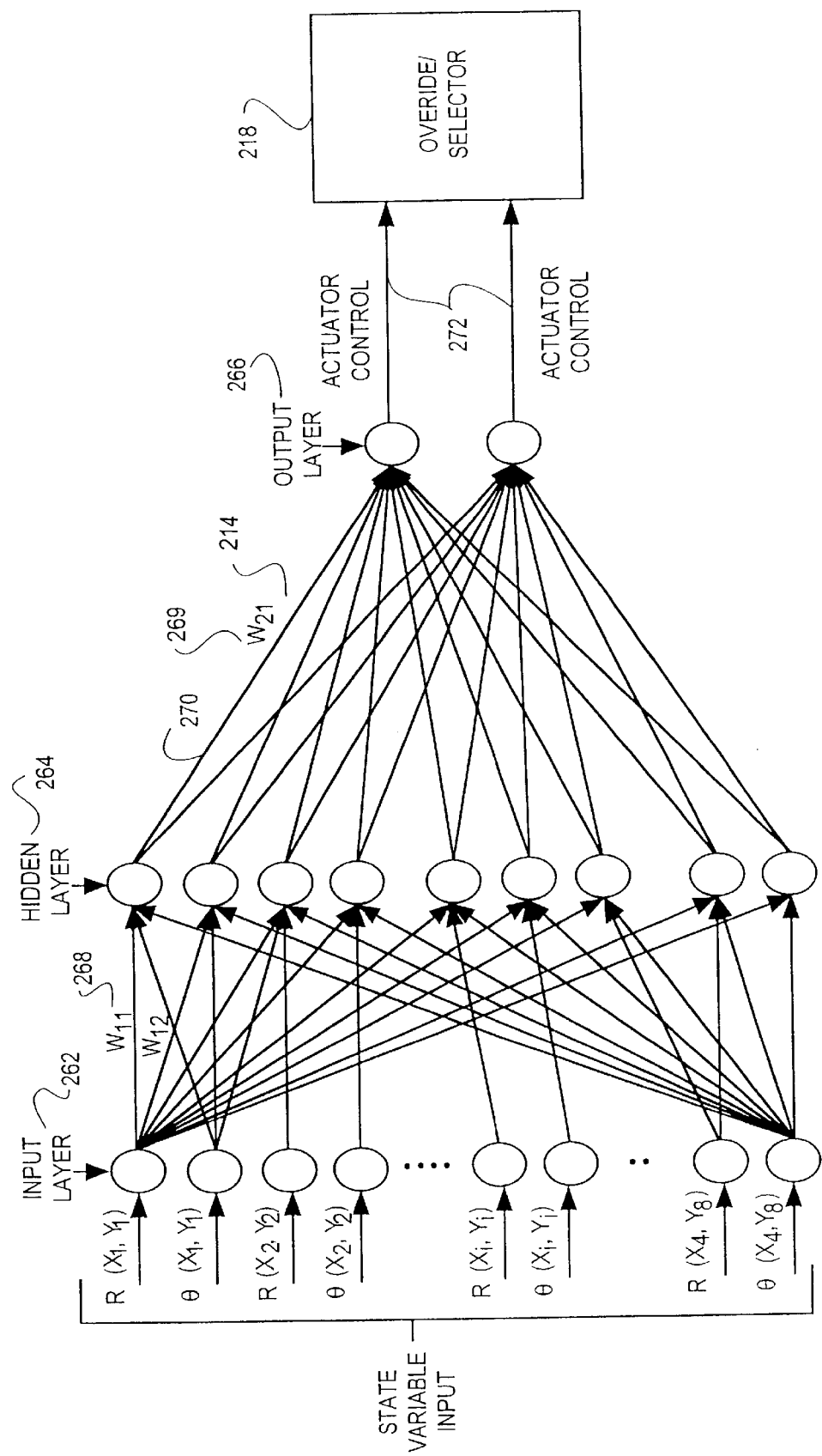
FIG. 20 illustrates a neural network controller utilizing the flow vectors of FIG. 19 to calculate controller outputs designed to effect a treatment (response) strategy; in the example shown, the timed injection of a measured amount of a drug such as nitroglycerin or epinephrine. (It will be apparent that the particular type or types of therapeutic agent used will depend upon the patient's condition and medical history, and may include anticonvulsive drugs, insulin or the like in appropriate cases.)

A more detailed illustration of the neural network controller 214 with the vector input of FIG. 19 is given in FIG. 20. The particular neural network illustrated is of a conventional type with multiple interconnected neurons arranged in successive layers. The input vector values are connected to input layer neurons 262 in the manner illustrated. Individual neurons are connected with links providing weights $W_{ij}$ for proper operation of the network. For simplicity, not all of the connection links or weights are shown. Outputs of the input layer 262 are connected to the hidden layer neurons 264 through weights 268 which in turn are connected to the output layer neurons 266 through weights 269 in any manner known to those skilled in the art of neural network design. A total of 64 inputs will be required for the neural network of FIG. 20 to accommodate the magnitude and angular coordinate directions of the vectors of FIG. 19. (It will be understood that more than one hidden layer may be used, if desired.) The neural network of FIG. 20 contains actuator control outputs 272 to control the position of catheter 232 in the manner illustrated in FIG. 18. The actuator control outputs 272, for example, may control drug injection and defibrillation in the patient 230 to maintain the state variables within the acceptable region 242. The actuator control signals 272 are fed to the override/selector controls 218 and 222 as shown in FIGS. 18 and 20 for connection to actuators 210 and 212 for control of the injector and scanning mechanism.

Training the neural network controller 214 of FIG. 18 may be accomplished using the "back propagation learning rule" described in the Lippman and Widrow articles identified above. Training inputs can be provided by actual control signals 207 supplied by the manual injection and scanning control 206 operated by the doctor 204 of FIG. 18. Such signals record actual doctor control action in response to changes in the state variables as captured by the input device 236. Error signals are generated corresponding to the opposite actual injection and/or defibrillation actions. For example, if the doctor caused physical movements $h_x$ and hy of the drug injection and defibrillation equipment, error signals $-h_x$ and $-h_y$ will represent the opposite of the actual movement of the equipment by the doctor 204. In this manner, with the state vectors as inputs, backward propagation may be used to train the neural network controller 214 to produce output control signals equal to the opposite of the actual physical movement of the devices caused by the doctor 204. The catheter actuator 218 of FIG. 18 may then be used to produce these actual physical movements in response to neural network outputs during execution of the actual medical procedure.

Figure 22:
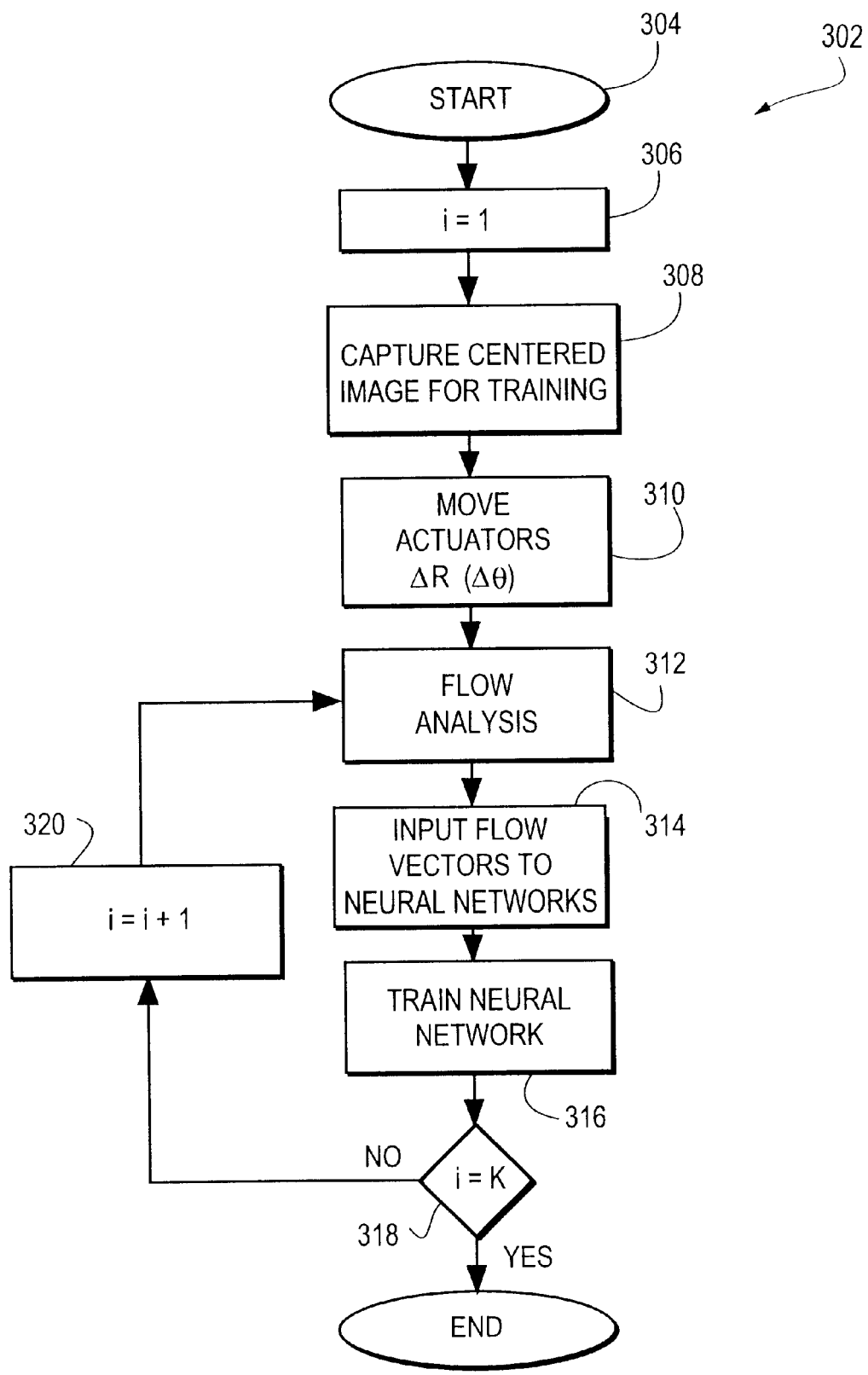
FIG. 22 is a flow chart for generation of training signals using actual patient responses.

In addition, or alternatively, the method of FIG. 22 may be used to train the neural network controller 214 of FIG. 18. In FIG. 21, a single frame 280 of data is captured under the control of the doctor 204 using control signal 203 of FIG. 18. The captured image represents the doctor's chosen values of the state variables. (It will be understood that the term "image" as used herein may refer to a video image, as above, or to a particular configuration of state variables as in the discussion below. In the latter usage of the term, "movement" of the "image" is simply a convenient way of referring to a change in the state variables. Which state variables are involved will depend on the medical condition of the patient and the range of treatment modalities selected for the system.)

Training signals for the neural network controller 214 may be generated by control computer 238 using simulated changes in the state variables. A frame 280 captured by input device 236 is stored in the memory of the control computer 238. The computer generates vectors that should occur if the frame 280 would move in selected directions in the variable space. This procedure can be accomplished within the memory of computer 238, generating vectors corresponding to different simulated changes of position of the frame 180 captured by the doctor or physician.

For example, as illustrated in FIG. 21, a set of eight movements in different directions $D_1, D_2, D_3, \ldots D_8$ may be generated. The proper correction control signal is generated by the neural network 114 and is opposite to the simulated movement of the frame 280. For example, if the frame 280 were moved x units to the "right," that is in the direction of $D_4$, then the corresponding desired output from the neural network 214 in response to the vectors generated from the simulated movement will be x units to the "left," or just the opposite of the change in state that generated the simulated vectors. In this manner, the neural network may be trained to compensate for changes in the state variables of blood pressure and heart rate.

This training procedure is outlined more particularly in the flow chart 282 of FIG. 21. In block 284 the training procedure is initialized by setting a counter, i=1. The physician then captures the training image in block 286. A control loop is then entered with simulated movement of the image in each of the respective directions from i=1 to i=K. For each simulated movement, the vectors are computed in block 290 and the corresponding corrections are computed in block 294. The vectors with their corresponding corrections are recorded in a position file 292 as indicated in the flow diagram 282. When the training simulator has indexed all K relative movements, neural network training is commenced in block 298.

As described above, training can be accomplished using, for example, the "back propagation learning rule" described in the Lippman and Widrow articles identified above. In general, an error signal can be defined as equal to the sum of the squared errors of the desired network outputs and the actual outputs. A gradient vector is then obtained by calculating backwards through the network, and the processing element weights of FIG. 24 are optimized to minimize the sum of the squared errors over the input image set.

Alternatively, or in addition to the simulation training method described above, actual changes in state variables and physician-dictated responses may be used to train the neural network 214 of FIG. 18. FIG. 22 illustrates a flow-chart 302 for training with such actual changes in state variables. In the diagram of FIG. 22, a total of K predetermined movements are used. In one embodiment, the simulation method of FIG. 21 may be used prior to the actual physical training of FIG. 22 to decrease convergence time of the overall training process. On line training may also be used with actual changes in state variables. and response by the doctor used to train the neural network.

In the flowchart 302 of FIG. 22, the training commences at start block 304. A counter "i" is set equal to 1 in block 306. The doctor 204 captures the training image in block 308 with the state variables within acceptable (target) limits. image properly positioned in the image field. The state variables are moved under program control in block 310 by an amount $\Delta R(\Delta \Phi)$. The correct neural network output will be the opposite of this movement to return the state variables to the selected position with the net vectors returned to zero or close to zero. Thus the neural network weights will be adjusted to result in this corresponding correction. The vectors are computed in 312. The values are input to the neural network in 314, with training and network weight adjustments taking place in 316. The training is continued using test 318 and counter increment 320 until the programmed K iterations have been made.

It will be understood that, in addition to back propagation training techniques such as those described above, other techniques known to those skilled in the art can be employed. For example, Hopfield neural networks may be employed, if desired.

The above described training procedures permit the doctor to select a desired acceptable range of state variables and train the system to hold the variables within that range. The system 200 maintains correct values of state variables automatically.

In general, expert systems using fuzzy logic methods are well known, as described in the following publications, each of which is incorporated herein by reference: Gottwald, Siegfried, *Fuzzy Sets and Fuzzy Logic: The Foundations of Application—from a Mathematical Point Of View*, Vieweg & Sohn, Braunschweig Wiesbaden (1993), ISBN 3-528-05311-9; McNeill, Daniel, *Fuzzy Logic*, Simon & Schuster, New York (1993), ISBN 0-671-73843-7; Marks, Robert I. II, *Fuzzy Logic Technology and Applications*. IEEE Technology Update Series (1994), ISBN 0-7803-1383-6, IEEE Catalog No. 94CR0101-6; Bosacchi, Bruno and Bezdek, James C, *Applications of Fuzzy Logic Technology*, Sep. 8–10, 1993, Boston, Mass., sponsored and published by the SPIE—The International Society for Optical Engineering, SPE No. 2061, ISBN 0-8194-1326-7; Rao, V. B. And Rao, H. V., *Neural Networks & Fuzzy Logic*, MIS Press, New York, 1995; Cox, E., The *Fuzzy Systems Handbook*, Academic Press, London, 1994; and, Chen, C. H., *Fuzzy Logic And Neural Network Handbook*, McGraw-Hill, New York, 1996.

Figure 23:
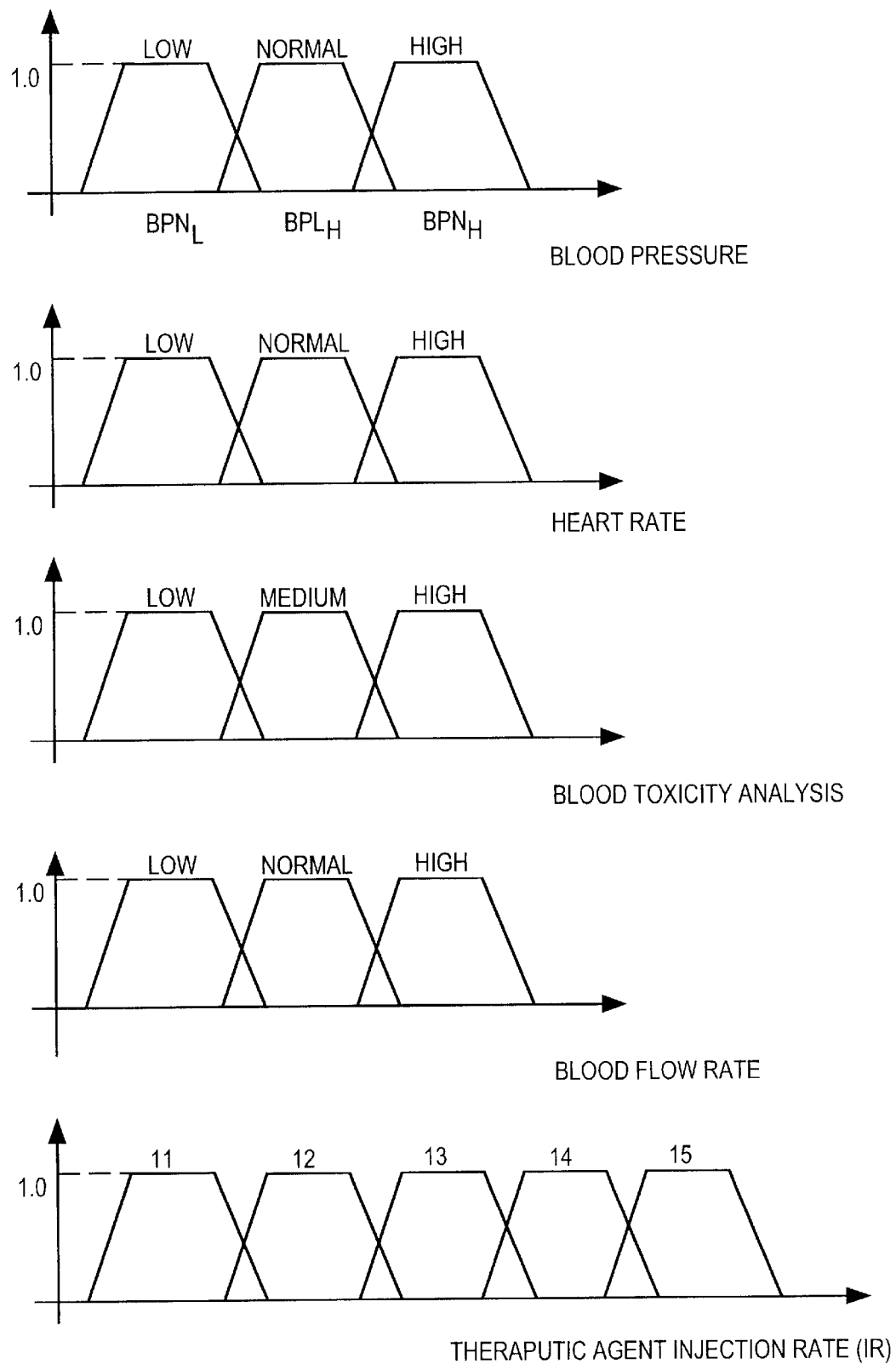
FIG. 23 illustrates possible fuzzy logic membership functions useful in selecting an appropriate drug injection program (or other treatment program) based on medical considerations as well as patient location information and real-time data concerning availability of various types of assistance.

Example sets of fuzzy logic variables and corresponding membership functions (MFs) are illustrated in FIG. 23. One embodiment of the fuzzy logic controller is implemented using trapezoidal fuzzy membership functions as shown in FIG. 23. Other membership functions (MFs) are possible including: (1) triangular MFs, (2) Gaussian MFs, (3) generalized bell MFs, and (4) sigmoidal MFs, any of which can easily be substituted for the trapezoidal fuzzy membership functions. Blood pressure, heart rate, blood toxin analysis results and/or blood flow rate are monitored in accordance with known principles of fuzzy logic. Standard IF . . . THEN inference rule constructs are used to derive a proper output for the therapeutic agent injection and/or scanning controls with fuzzy membership as shown in illustration 310 of FIG. 23.

The blood pressure membership function of FIG. 23 may be determined directly by image analysis computer 238 and may represent systolic or diastolic pressure or some combination thereof, with or without moving time averaging applied.

The blood toxin (BT) analysis membership function of FIG. 23 is derived in blood analysis computer 234 and may be based on samples of blood drawn from arteries leading to or from the diseased area, or a combination of both. Indication of high levels of toxicity may require restriction of injection of certain therapeutic agents. Similarly the blood flow rate fuzzy membership 308 of FIG. 23 may be derived using image analysis computer 238, or that computer in combination with blood analysis 234. If blood toxin levels exceed acceptable levels, safety limiter 224 is activated to stop the flow of therapeutic agents and blood analysis computer 134 activates alarm 228.

Application Of Fuzzy Logic Membership Functions

As shown in FIG. 23, the trapezoidal fuzzy logic membership functions include overlapping membership ranges for the following variable ranges:
BLOOD PRESSURE: LOW, NORMAL AND HIGH
HEART RATE: ZERO, LOW, NORMAL AND HIGH
BLOOD TOXICITY ANALYSIS: LOW, MEDIUM AND HIGH
BLOOD FLOW RATE: LOW, NORMAL AND HIGH
THERAPEUTIC AGENT INJECTION RATE: $I_1$ through $I_5$ (in order of increasing injection rate)

To better understand the fuzzy logic compositional rules applied to the patient monitor fuzzy reasoning system and method, consider first just the blood pressure variable shown in FIG. 23. The fuzzy set corresponding to "LOW" blood pressure is the set of all blood pressures BP between zero and the upper blood pressure $BPL_H$ defined for low blood pressures. Similarly, the fuzzy set corresponding to "NORMAL" blood pressures is the set of all blood pressures between the lowest defined "NORMAL" blood pressure $BPN_L$ and the upper normal blood pressure $BPN_H$. Because of the "fuzzy" definitions of "normal blood pressures" and "low blood pressures," it will be true that $BPN_L < BPL_H$ and the fuzzy sets will overlap. Similarly, for example, overlap occurs between the defined "Normal" and "High" blood pressure ranges. The nature of the overlapping membership functions for several of the variables involved in the disclosed fuzzy injection controller are illustrated in FIG. 23. Similar relationships would exist for the other variables.

Application Of Fuzzy Logic Inference Rules

The fuzzy logic rule base for the system and method for treating select tissue in a living being disclosed herein is formulated with "IF . . . THEN . . ." structures representing the linguistic expression of the logical elements involved in the fuzzy logic rule base. Depending on the fuzzy logic inference rules determined by physicians, the therapeutic agent injection membership function 210 is defined. Using known fuzzy logic implementation methods, different inference rules will result in different levels of therapeutic agent injection. As explained above, the same is true of defibrillation; with specific reference to the fuzzy logic membership functions pertaining to the availability (location, source and estimated time of arrival) of human medical assistance.

FIG. 24 illustrates exemplary simple fuzzy logic inference rules for the particular embodiment discussed. In the example given, each of the state variables are assumed to take on their ranges of values—Low, Normal and High or other values as specified. For each of the corresponding combinations of blood pressure and heart rate, the therapeutic injection rate (IR) is specified for the ranges of blood pressure (BP) and heart rate (HR) variables of FIG. 23. A total of 27 rules are specified in FIG. 24. Three additional sets of rules (not shown) would exist for the additional blood toxicity, blood flow rate and scanning functions. Example linguistic expressions of the rules in the tables of FIG. 24, at are:

IF BP=L AND HR=L, THEN IR=$I_5$;
IF BP=H AND HR=N, THEN IR=$I_3$.

of course, in practice the inference rule relationships between the injection rates and other variable values will be defined by the physician or specialized experts in the treatment procedure being used. In fact, such rules may be varied depending on the individual patient's medical history, doctor or particular disease characteristics and treatment requirements. It should be understood, therefore, that the particular inference rule relationships shown in FIG. 24 are for purposes of illustration only.

The above rules are structured using the input values for each of the individual variables combined with logical "AND" operators. The use of the "AND" operator ensures that all of the variables are in the acceptable ranges. When multiple input variable combinations map into the same output subset, then membership in that subset is the minimum of the individual membership functions as follows:

$U_k(IR) = \min \{U_i(BP), U_i(HR), U_i(BT), U_i(BF), U_i(ETA)\}$

Using these weighted membership functions, defuzzification methods known to those skilled in fuzzy logic system technology, such as the centroid method, may be used to derive the actual appropriate therapeutic agent injection control values based on the membership functions illustrated in FIG. 23 and the rules illustrated in FIG. 24.

While neural network controllers and fuzzy logic may be used in the above described manner to control and maintain the state variables within the desired (nominal) range, such control is not a total replacement for the skilled hands and judgment of the doctor 204 treating the patient 230. For these reasons, override 218 and 222 of FIG. 18 are important system elements and permit the doctor 204 to take control of the procedure at any time.

Steerable Catheters

FIGS. 4 through 7 and 18 illustrate several catheter steering mechanisms designed to control the shape of the catheter inside the body. Conventionally, this is accomplished by tensioning and relaxing mechanical pull wires. Such arrangements, however, provide a limited range of shapes and typically can bend at only one predetermined inflection point along the length of the catheter. The devices disclosed below overcome those disadvantages.

Figure 4:
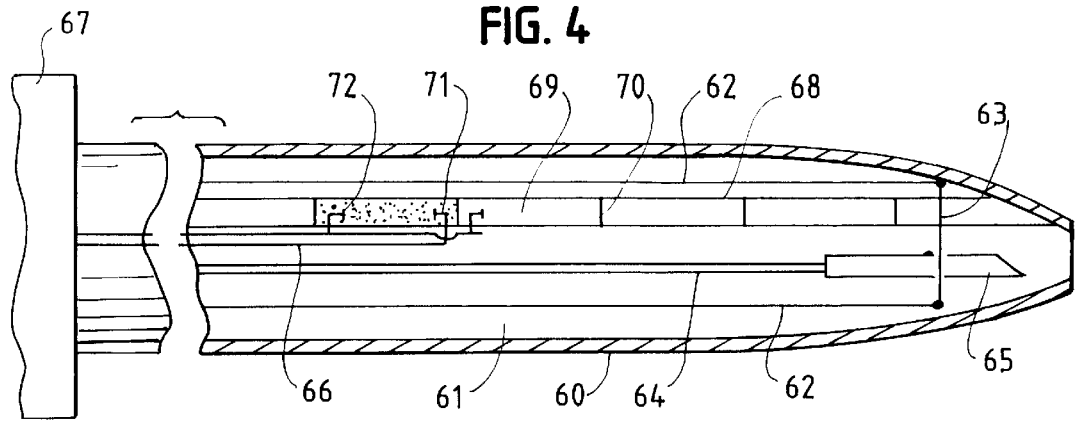
FIG. 4 shows a steerable catheter system (which can utilize real-time external computer imaging control system to find and maintain a position in the body adjacent the volume of tissue to be diagnosed or treated) wherein a steering mechanism for the catheter uses pull wires combined with an electrically-controllable stiffening member using an electrorheological gel.

Referring initially to FIG. 4, a medical instrument such as a catheter 60 having one or more internal lumens 61, is shown as containing one or more pull wires 62 affixed to a plate 63 near the distal end of the catheter. The lumen also may contain one or more of any number of operating mechanisms 64 (an extendable hollow needle 65 is illustrated, but many other operating mechanisms can be used), including such devices as biopsy devices, microwave or RF waveguides, chemical sensors and the like). Also included inside the lumen 61 is a controllable stiffening member 68, which may take the form of a longitudinally-extending tube having one or more longitudinally-extending compartments 69 separated at intervals by walls 70. Inside each compartment is a quantity of an electrorheological gel (ER gel), which is a gel that exhibits a phenomenon called the Winslow effect, or a magnetic gel, such as ER gel or fluid materials typically comprise a dielectric fluid in which is dispersed a plurality of microscopic electrorheologically sensitive particles. Application of an electrical field to such a composite material alters the pattern of electrical charge distribution on the surface of the electrorheological particles, causing them to be attracted to each other and to become aligned in a regular fashion, effectively forming chains of microscopic fibers between the electrodes. The electrorheological particles may include silica, starch, carboxy-modified polyacrylamides, and similar materials which will function only in the presence of some water. Other materials such as organic semiconductors, including silicone ionomers, are capable of functioning as ER gels without water. See, for example, U.S. Pat. No. 4,772,407 (Carlson); U.S. Pat. No. 5,032,307 (Carlson); U.S. Pat. No. 5,252,249 (Kurachi, et al); U.S. Pat. No. 5,252,250 (Endo, et al); and U.S. Pat. No. 5,412,006 (Fisher, et al), the disclosures of which are incorporated by reference herein. Melted chocolate also has been shown to exhibit ER gel properties.

When exposed to an electrical potential gradient, ER gels exhibit a macroscopic change from liquid-like behavior to essentially solid behavior. That is, the ER fluids or gels change from behaving as Newtonian fluids, which deform continuously and without limit in response to the application of any stress (force) at all, to Bingham plastic fluids, which will not deform at all until some threshold level of yield stress (force) is applied. The yield stress is often very high, resulting in the gel exhibiting essentially solid behavior.

Inserted into each compartment 69 of stiffening member 68 is an activating electrode 71. The compartments may share a common ground electrode 72, or separate pairs of electrodes may be used in each compartment. In either case, when an electrical potential is applied through wires 66 from controller 67 across any given compartment, the ER gel in that compartment solidifies (typically within a few milliseconds), thus making that portion of stiffening member 68 rigid. In that fashion the stiffness or pliability of each of the compartments 69 of stiffening member 68 can be electrically controlled. Thus, any portion of the length of the catheter can be made stiff or pliable, as desired. This changes where the catheter will bend in response to the off-center forces imposed by pull wires 62. In this fashion the shape of the catheter can be changed as desired, producing one or more straight sections and one or more bent sections. Further, when the desired curvature has been attained, all compartments of the stiffening member 68 can be electrically energized, thus "freezing" the catheter in the desired shape for as long as the electrical potential is applied. Such electrical control technique used by the ER gel in this type of catheter makes it particularly attractive for use in combination with a computer-controlled positioning system of the general type shown in FIGS. 1–3, above.

Figure 5:
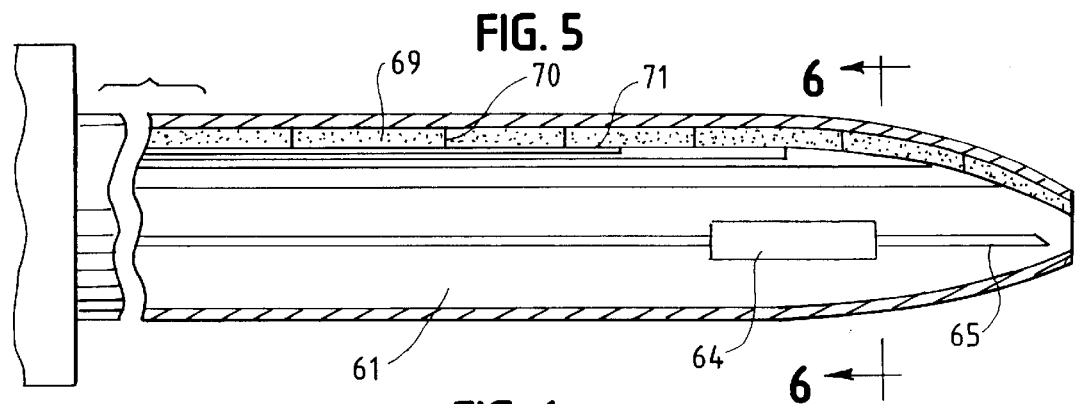
FIG. 5 shows an alternative arrangement of a steerable catheter using an electrorheological gel.
Figure 6:
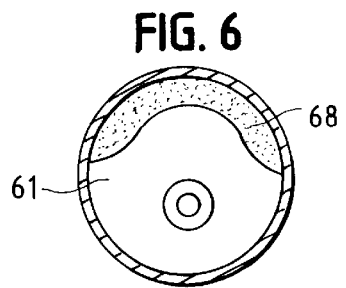
FIG. 6 shows a cross-sectional view of the steerable catheter of FIG. 5.

FIGS. 5 and 6 illustrate an alternative embodiment of a steerable catheter using ER gel. In this embodiment, the stiffening member 68 is formed as a full or partial annular space along the interior wall of the lumen 61. In many instances this may be a preferable arrangement from the standpoint of conserving interior space and reducing the size of the catheter.

Figure 7:
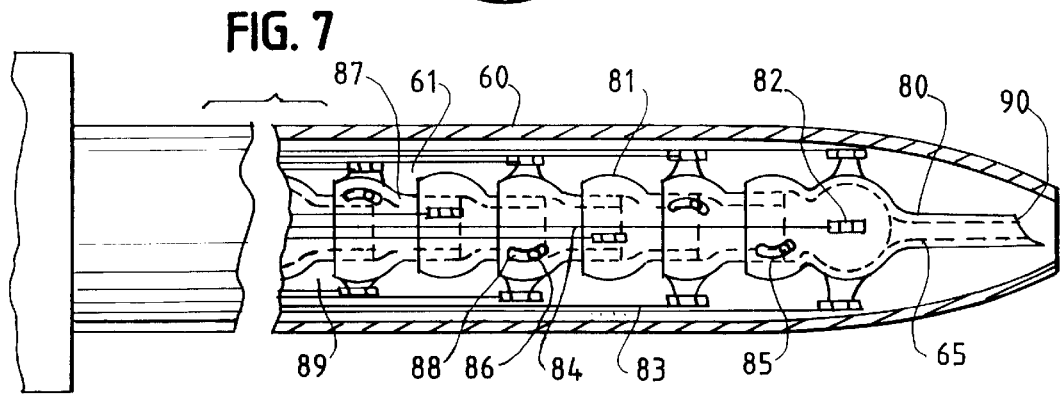
FIG. 7 illustrates a steerable hollow needle mechanism is suitable for injecting drugs, which can be introduced through a pliable catheter.

FIG. 7 illustrates an alternative mechanical steering arrangement, specifically designed for administration of drugs. In this design, a hollow needle 65 is attached to the distal end of a line of universally rotatable members 81. (Any form of fluid-tight, universally rotatable member can be used; the preferred arrangement is the ball and socket joints depicted in FIG. 7.) The ball and socket joints are hollow, providing a continuous fluid-tight passageway 82 through the center of the line of ball and socket joints. (One specific structure for such ball and socket joint fluid conduits is explained in U.S. Pat. No. 5,449,206 (Lockwood), the disclosure of which is incorporated by reference herein.) At intervals along the length of the line of ball and socket joints, pull wires 83 and 84 are attached to the exterior of the joints. Preferably four sets of pull wires are used, as shown, providing the ability to steer the line of ball and socket joints in any direction. Further, additional pull wires may be affixed at more than one longitudinal location (also as shown), which provides capability of bending the line of ball and socket joints at different longitudinal positions.

Still further, a plurality of optional pin and slot arrangements 85 can be used to prevent the individual ball and socket members from rotating with respect to each other. (The pins 86 are attached or molded to the exterior surfaces of the smaller or male balls 87 and protrude through slots 88 in the larger or female sockets 89 in the adjacent members.) The pin and slot arrangements permit the line of ball and socket joints to transmit torque; and also prevent the pull wires from becoming tangled since the individual members cannot rotate with respect to each other.

Another feature of the device shown in FIG. 7 is a rupture disk 90 which blocks the distal end of hollow needle 65. The purpose of the disk is to prevent the flow of body fluids back into the passageway 82 during introduction of the catheter. This discourages clot formation and eliminates the need to flush the passageway with heparin or some comparable anti-clotting agent. The rupture disk 90 is designed to rupture when exposed to sufficient fluid pressure through passageway 82, permitting flow of the liquid drug into the select area of tissue. (Alternatively, disk 90 may be a low melting point material that is opened by application of electrical resistance heat or laser energy thereto.)

Still another alternative to the use of an extendable hollow needle is a fluid jet injection system, which uses the high velocity of the fluid itself to penetrate tissue.

Steering systems of the foregoing types require internal pull wires or other internal structures, which occupy space within the lumen of the catheter. Desirably, however, the catheter diameter should be as small as possible to minimize insertion trauma and unwanted damage to surrounding tissue.

FIG. 11 illustrates a steerable diagnostic imaging catheter that works without any internal steering mechanism. The walls of the catheter include a plurality of compartments which include ferromagnetic materials or strong magnets or, more preferably, wound electromagnets. A patient who is to receive this catheter is placed inside a strong, controllable electromagnet. Once introduced into a patient, the position of the catheter can be adjusted by varying the direction and magnitude of the externally-applied magnetic field, thus pulling the catheter in any desired direction within the patient's body. If small electromagnets are used in the catheter walls themselves, only a desired part of the catheter length can be made responsive to the externally-applied magnetic field, thus making it possible to selectively shape the catheter inside the patient. Alternatively, a single annular magnet or piece of ferromagnetic material can be moved longitudinally along the interior wall of the catheter to alter the point of application of the external electromagnetic force.

The catheter of FIG. 11 also includes a lens 91 transpiercing the wall of the catheter and a plurality of fiber optic cables 92 operably attached to the lens, to transmit images or visual information back to external sensor (not shown), located outside the body. Visible light or laser energy also can be transmitted through the optical fibers for purposes of illumination and/or ablation of select tissue such as cancerous tissue and tumors. A flushing nozzle 94 supplied through a lumen 95 may be used to keep the lens 91 clear, if desired, by flushing with saline or some other benign, inert clear fluid, under computer control. (Various specific optical fiber arrangements are known in the art, as shown for example in U.S. Pat. No. 4,967,745 (Hayes, et al.), the disclosure of which is incorporated by reference herein.)

Because of the need for controllable magnetic fields for catheter positioning in this embodiment, MRI imaging techniques may be unsuitable unless MRI imaging and catheter position are conducted intermittently. Ultrasonic imaging, of course, can be used. A cavity 96 can be provided in the distal end of the catheter to provide an enhanced ultrasonic image of its location.

In the treatment of certain conditions such as cancerous tissue, the local application of heat has been found desirable. Eddy current heating of a catheter having a positionable insert made of ferromagnetic material can be used for that purpose. A rapidly varying and/or focused external magnetic field is applied to cause the heating.

Figure 8:
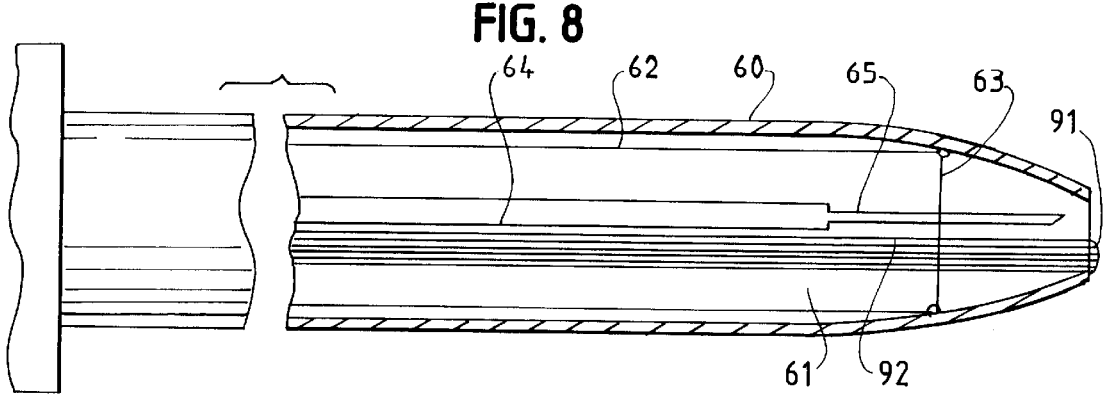
FIG. 8 shows a steerable catheter system utilizing real-time computer control based on internal imaging techniques to find and maintain the operating head of the catheter at a position in the body adjacent the volume of tissue to be diagnosed or treated.

FIG. 8 illustrates a catheter using pull wire steering wires, which catheter has been adapted to carry a lens 91 and fiber optic bundle 92 alongside an operating mechanism 64 (in this instance an extendable hollow needle 65). Such a catheter can be controllably positioned using a combination of external imaging and computer analysis of the images provided by lens 91 and fiber optic bundle 92. It will be apparent to those of ordinary skill that the external magnetic steering mechanism or the ER gel steering mechanism described above also may be used in this type of catheter.

Figure 9:
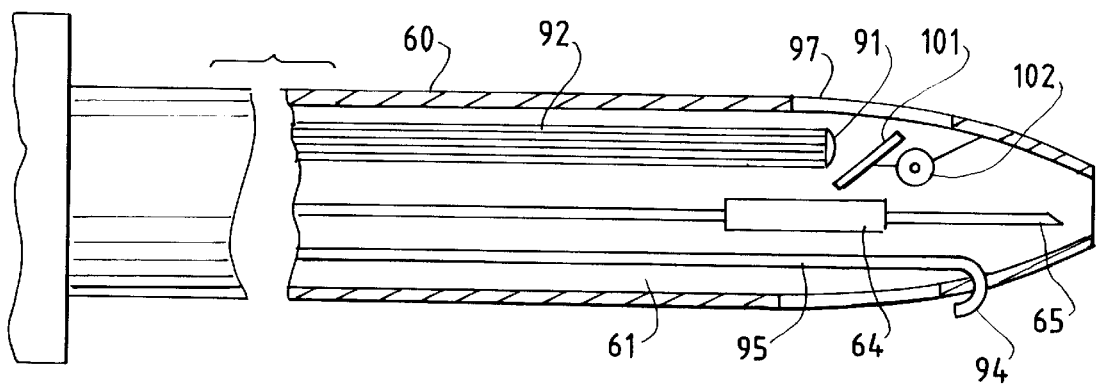
FIG. 9 shows a variation on the steerable catheter system of FIG. 8, wherein the internal imaging system can be operated to provide a 360° view around the circumference of the distal end of the catheter.

It may be desirable to be able to adjust the viewing direction of a fiber optic bundle at the distal end of a catheter. FIG. 9 illustrates one possible arrangement for accomplishing that goal. In this catheter, a rotatable mirror 101 driven by a micromotor 102, is used to direct the axis or angle of view of a lens 91 in any desired direction out a clear window 97 in the wall of the catheter. A flushing nozzle 94 assists in clearing the surface of window 97. Any of the steering mechanisms described above may be used with this arrangement of internals, as well.

Figure 10:
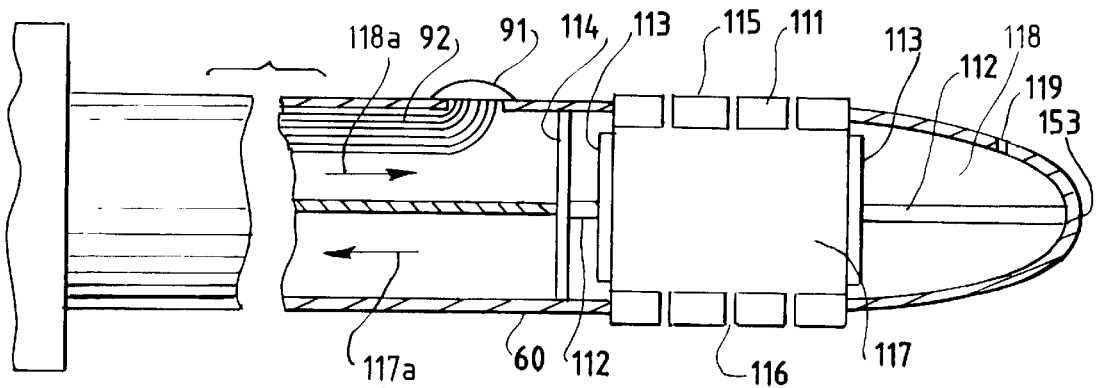
FIG. 10 shows a steerable catheter system in which an expandable, rotatable abrasive member actuated by an external magnetic field is used as a device for removal of plaque from the interior of blood vessels.

A variety of procedures including angioplasty require the ability to operate abrasion devices within blood vessels or other body ducts. Typically this requires insertion of drive mechanisms through the lumen of a catheter. FIG. 10 shows an alternative arrangement in which a catheter 60 is fitted with a rotary abrasion member 111 mounted on central axle 112 and having an abrasive outer surface 115. Rotary abrasion member 111 is axially supported between the distal end 153 of the catheter and internal support member 114. Magnets 113 are mounted at either or both ends of the cylindrical rotary abrasion member.

In operation, after the catheter has been introduced and positioned, an intermittent or rotating external magnetic field is applied from electromagnets outside the patient's body. This field engages magnets 113 and turns rotary abrasion member 111, causing the mechanical abrasion of surrounding tissue. Optionally, a lens 91 and fiber optic assembly 92 may be used to observe the operation. Further, a plurality of fenestrations 116 may be provided, transpiercing the rotary abrasion member 111. Blood or body fluids (supplemented with a saline flush, if desired) may be aspirated through fenestrations 116 into lumen 117 of the catheter, carrying away particles of plaque or other abraded material. The saline flush can be supplied through another lumen 118 of the catheter, and out through fenestrations 119 in the distal end of the catheter. The general direction of fluid flow is shown by arrows 117a and 118a. This simple device offers positive mechanical abrasion with minimal trauma because of the small diameter of the catheter. Steering of the catheter can be accomplished using external magnetic fields as well, or one of the mechanical steering mechanisms disclosed above can be used.

In treating a variety of diseases, it is desirable to be able to apply controlled doses of therapeutic drugs to select tissue without exposing nearby tissue to the same drugs. Chemotherapeutic agents used in cancer treatment, which may be rather toxic, are one example.

FIG. 12 illustrates a catheter suitable for directing a measured aliquot of liquid drug to a specific target location in the body. In this design, a reservoir 120 containing a pre-measured aliquot of liquid drug is positioned near the end of catheter 60. Reservoir 120 is attached to the distal end of an extendable member 121, which is used to extend the hollow needle 65 into the tissue surrounding the distal end 53 of the catheter through an orifice 122. Release of the drug from reservoir 120 is accomplished by rotating extendable member 121, which releases a catch mechanism 123, allowing a compressed spring 124 to expand, forcing piston 125 forward and discharging the drug through optional rupture disk 90. Positioning of the catheter can be accomplished using the computerized positioning system described above, in conjunction with the pull wires 62 shown in FIG. 12 or another of the steering systems disclosed above.

FIG. 13 illustrates an alternate embodiment in which a hollow needle 65 is extended by a micromotor 130 operating on a gear line 131 on the exterior of reservoir 120. Some control of the angle of insertion is achieved by micromotor 132, which moves the distal end 133 of reservoir 120 up and down in the lumen 61.

Figure 14:
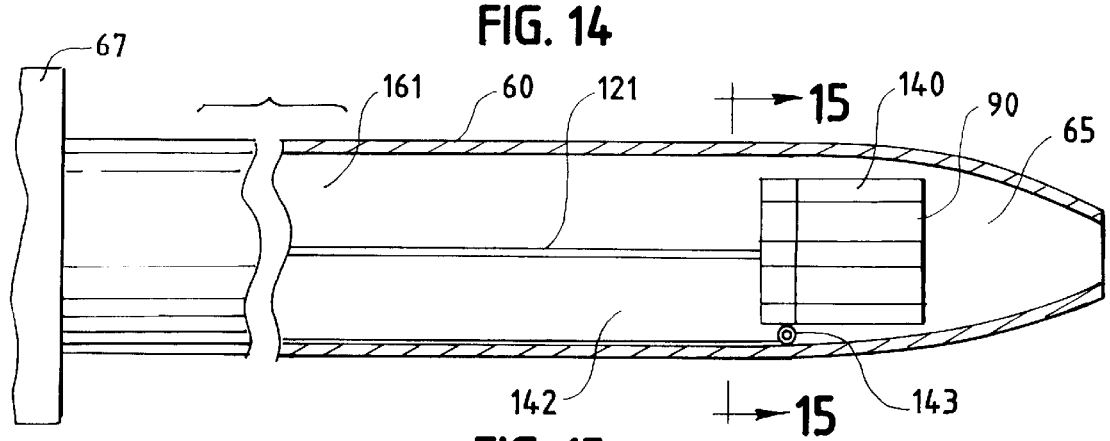
FIG. 14 shows a catheter system (optionally, steerable under computer control) having a multidose drug delivery system.
Figure 15:
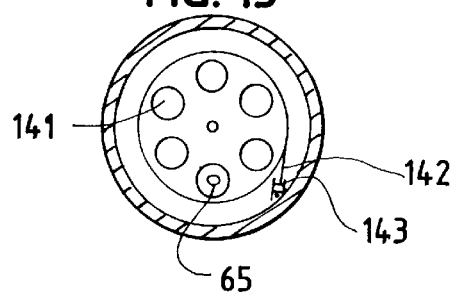
FIG. 15 shows a cross-section of the catheter including the multidose drug delivery system shown in FIG. 14.

In some instances it may be desirable to be able to inject multiple doses of drugs without removing the catheter from the body. FIGS. 14 and 15 illustrate a device capable of providing a plurality of injections of individual aliquots of drug, which may have different compositions. This system uses a rotatable cylinder 140 containing a plurality of individual reservoirs 141. Operation of the device may be similar to that of a revolving pistol. The rotatable cylinder 140 is rotated by pulling on a rotating wire 142, which is wrapped around the cylinder and then passes over a block 143, which leads wire 142 back toward the proximal end of the catheter. Each individual reservoir 141 is fitted with a rupture disk 90, or other type of controllable valve preventing premature discharge of the drug. Extension of hollow needle 65 is accomplished by extendable member 121, as in the embodiment of FIG. 12. Discharge of the drug is accomplished by individual spring piston arrangements in each reservoir, like that shown in the embodiment of FIG. 12. Any of the steering mechanisms disclosed above also can be employed, if desired.

Figure 16:
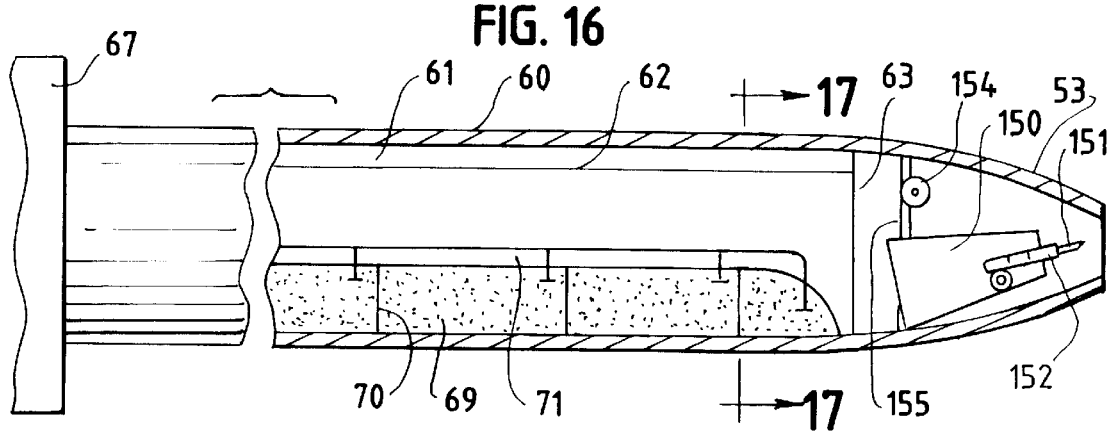
FIG. 16 shows a steerable catheter having a telescoping stylet suitable for the controlled delivery of RF energy to surrounding tissue.
Figure 17:
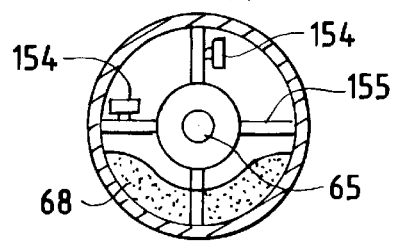
FIG. 17 shows a cross-section of the steerable catheter of FIG. 16.

As noted above, it may be desirable to apply RF or microwave energy to specifically identified select tissue areas. FIGS. 16 and 17 provide an illustration of such a catheter. In this catheter, steering is provided by a pull wire 62 in cooperation with a plurality of ER gel compartments 69, as described above in conjunction with the embodiment of FIGS. 5 and 6.

Inside the distal end 53 of the catheter 60 is an angulation mechanism 150. It comprises a telescopically extendable stylet 151 which is controllably operable as a microwave or RF antenna. The stylet is extended out of insulating sheath 152 by a reversible gear motor or a micromotor 153 (solenoid). The direction of extension of the stylet 151 is controlled in part by one or more micromotors 154, which are mounted on support grid 155 to provide angulation in any desired direction. Optionally, means (not shown) can be provided for also extending the insulating sheath as well as the conductive stylet. This helps protect surrounding tissue from the RF or microwave energy and further localizes the tissue destructive effect of such energy.

The performance of the catheters and other medical instruments of this invention can be improved by applying a coating that resists thrombogenesis, such as the coatings described in U.S. Pat. No. 5,514,409 (Maraganore), the disclosure of which is incorporated by reference herein.

Catheters For Controllable Scanning

Figure 25:
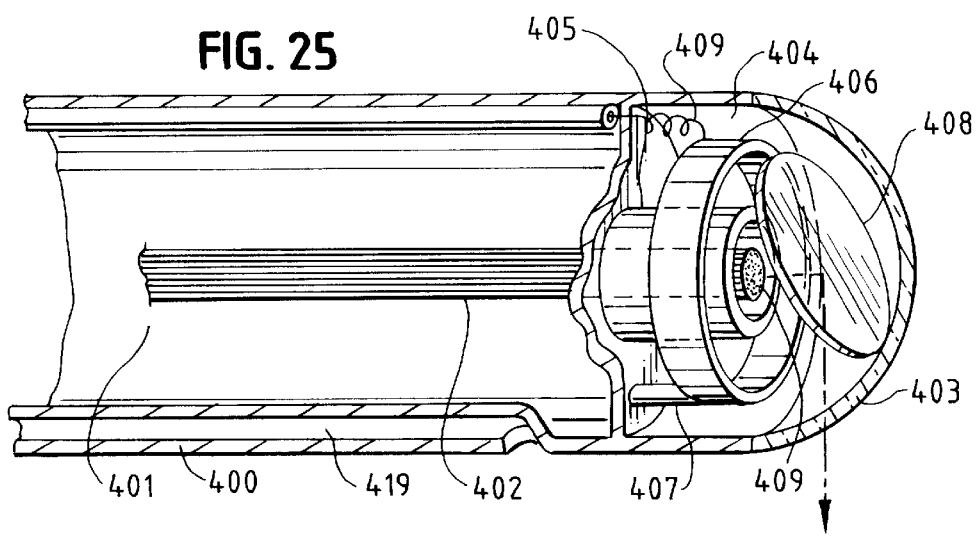
FIG. 25 shows another embodiment of a catheter suitable for providing laser light or non-coherent light in a controlled rotational scanning pattern.

For many applications, for example in photodynamic therapy, it is desirable to be able to controllably direct a beam of laser light, ordinary light or other radiation at select body tissue. FIG. 25 illustrates an embodiment of a catheter suitable for that purpose. The catheter 400 includes one or more internal lumens 401, through which passes a fiber optic array or light pipe 402 or other apparatus for supplying light. At the distal end of catheter 400 is a transparent lens 403, preferably hemispherical in shape. Inside the distal end of the catheter is a positioning motor assembly 404, preferably comprising a stepping motor. In the arrangement shown, the rotor 405 of the stepping motor is attached to the catheter 400. Surrounding coil 406 (referred to herein as the stator for consistency with standard terminology even though in this embodiment it is the stator that rotates while the rotor is fixed to the catheter) is free to rotate around the central axis of the stepping motor. The stepping motor may be provided with a mechanical stop 407 which limits rotation to 180 degrees, thereby preventing wires 409 from becoming wrapped around the central axis. Alternatively, a brush or wiper arrangement can be used to energize the coils in the rotor, permitting continuous rotation. Actuation of the stepping motor is accomplished by exciting various windings in sequence according to the amount of rotation desired.

Attached to the rotor 406 is a mirror 408, at an angle suitable to deflect a beam of light 409 issuing from the distal end 410 of the fiber optic array 402 out through the transparent lens 403. An angle of 45 degrees may be preferable, but other angles are also possible.

Figure 26:
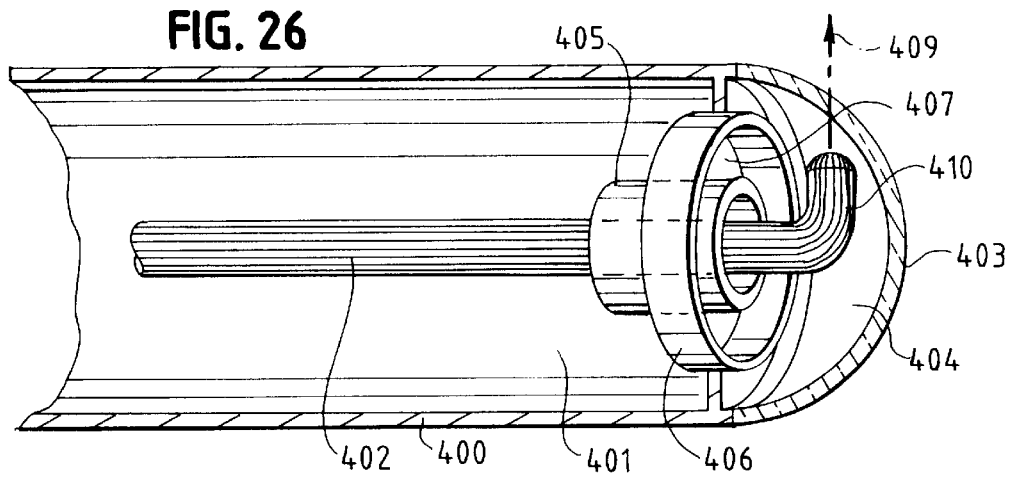
FIG. 26 shows another embodiment of a catheter suitable for providing laser light or non-coherent light in a controlled rotational and/or angular scanning pattern.

It will be understood that alternative devices for deflecting the light beam can be used. FIG. 26 shows one such alternative. In the embodiment of FIG. 29, the rotor 406 is affixed to the catheter 400. The fiber optic array or light pipe 402 is attached to the rotor 405 of the stepping motor 404. The distal end 410 of the fiber optic array is bent to deflect the light beam 409 at an angle to the catheter axis. Stop 407 restricts rotation of the stator, while the rotor remains fixed.

Figure 27:
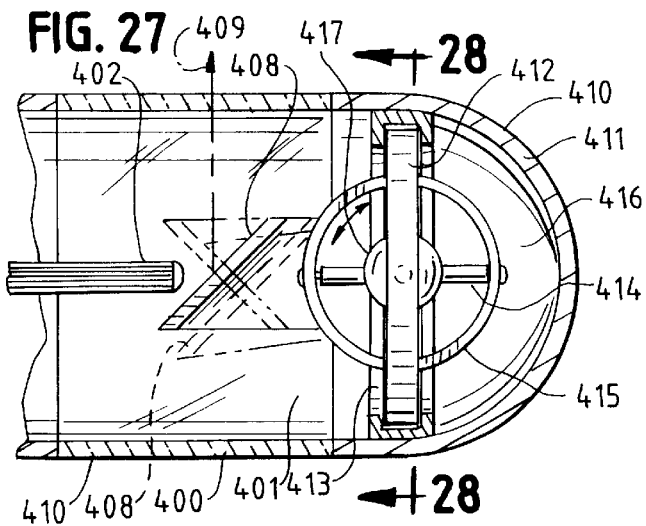
FIG. 27 shows still another embodiment of a catheter suitable for providing laser light or non-coherent light in a controlled rotational and/or angular scanning pattern.
Figure 28:
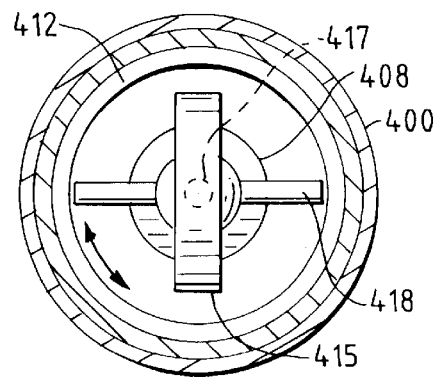
FIG. 28 shows a cross-section of the catheter of FIG. 27.

FIGS. 27 and 28 show another embodiment, in which the beam of light can be deflected or scanned both by rotation through 360 degrees and also by changing its angle relative to the axis of the catheter. In that fashion the light beam can be moved longitudinally with respect to the catheter axis.

FIG. 27 shows a catheter 400 with at least one lumen 401. The catheter includes a portion in which its wall is transparent. The transparent wall portion is preferably near the distal end 411 of the catheter, but can also be at other longitudinal locations if desired. The distal end of fiber optic array or light pipe 402 is directed toward mirror 408, which in turn is mounted on the stator 412 of first stepping motor 413. First stepping motor 413 is arranged to enable the stator to rotate the mirror 408 up to 180 degrees in either direction around the axis of the catheter, thus directing the beam of light in a circular path outward from the catheter.

Second stepping motor 416 is arranged to tilt the mirror 408 with respect to the axis of the catheter, thereby causing the beam of light 409 to traverse in a direction parallel to the catheter axis. In the embodiment shown, this is accomplished by affixing the rotor 414 of the first stepping motor 413 to the stator 415 of second stepping motor 416. The rotor 417 of the second stepping motor is, in turn, affixed to the catheter 400 through one or more braces 418, as shown in cross-section FIG. 28.

Although the distal ends of the catheters in FIGS. 25–27 are depicted as hemispherical, it will be understood that a more pointed distal end shape (especially for the embodiments shown in FIGS. 27 and 28) may facilitate percutaneous insertion.

FIGS. 27 and 28 show a single stepping motor and mirror arrangement. More than one such arrangement can be used at different locations along the length of the catheter, if desired, in order to provide light radiation at various locations.

In addition to the scanning mechanism shown in FIGS. 25–28, one or more additional lumens 419 can be used to carry drugs or other fluids, as shown in FIG. 25. Microminiature TV cameras, or fiber optic arrays transmitting images, also can be used. Further, the position control and steering mechanisms described above also can be combined with the scanning mechanisms disclosed in the embodiments of FIGS. 25–28 and similar scanning arrangements.

Although described in terms of light energy, the embodiments of this invention (and in particular, those of FIGS. 25–28) also can be used to controllably direct other forms of energy, including but not limited to X-radiation, ultrasound, ion beams, neutron beams, microwave radiation and the like. The form of waveguide needed will be known to those skilled in the art depending upon the particular type of radiation involved.

It will be apparent to those of ordinary skill in the art that many changes and modifications may be made while remaining within the scope of my invention. I intend to cover all such equivalent structures and methods, and to limit my invention only as specifically delineated in the following claims.

I claim as my invention:

1. A catheter for use in connection with an externally located magnetic field source comprising: an elongated tube having a proximal end and a distal end and a rotatable section with an abrasive outer surface and a magnetically susceptible member attached to said rotatable section, whereby said rotatable section is rotatable in response to a rotating magnetic field; and a lens directed toward said outer surface of said rotatable section for viewing the effect of rotation of the section; and at least one fiber optic cable attached to said lens, for transmitting visual information to a remote sensor.

2. The catheter of claim 1, further comprising (a) an outlet distal of said rotatable section; (b) a first lumen inside said catheter and extending from said proximal end of said catheter to said outlet; (c) a second lumen inside said catheter and extending from said proximal end to said rotatable section; (d) a plurality of fenestrations through said rotatable section communicating with said second lumen; and (e) means for supplying a flushing liquid to said first lumen and withdrawing said flushing liquid through said second lumen.

* * * * *